United States Patent
Brendel et al.

(10) Patent No.: US 6,177,449 B1
(45) Date of Patent: Jan. 23, 2001

(54) SULFONAMIDE-SUBSTITUTED CHROMANS, PROCESSES FOR THEIR PREPARATION, THEIR USE AS A MEDICAMENT OR DIAGNOSTIC, AND PHARMACEUTICAL PREPARATIONS COMPRISING THEM

(75) Inventors: Joachim Brendel, Bad Vilbel; Uwe Gerlach, Hattersheim; Hans Jochen Lang, Hofheim; Klaus Weidmann, Kronberg, all of (DE)

(73) Assignee: Aventis Pharma Deutschland GmbH, Frankfurt am Main (DE)

( * ) Notice: Under 35 U.S.C. 154(b), the term of this patent shall be extended for 0 days.

(21) Appl. No.: 09/421,277

(22) Filed: Oct. 20, 1999

Related U.S. Application Data

(63) Continuation of application No. 09/160,298, filed on Sep. 25, 1998, now abandoned.

(30) Foreign Application Priority Data

Sep. 26, 1997 (DE) .............................................. 197 42 508

(51) Int. Cl.⁷ ..................... A61K 31/445; A61K 31/35; A61K 31/38; A61K 31/44; C07D 401/00
(52) U.S. Cl. ..................... 514/320; 514/456; 514/444; 514/337; 546/196; 546/282.7; 549/404; 549/60
(58) Field of Search ............................ 549/60, 404, 331; 514/444, 456, 337, 320; 546/282.7, 196

(56) References Cited

U.S. PATENT DOCUMENTS

| 4,820,834 | 4/1989 | Evans et al. ......................... 540/504 |
| 5,082,858 | 1/1992 | Garcia et al. ......................... 514/456 |
| 5,151,442 | 9/1992 | Garcia et al. ......................... 549/456 |

FOREIGN PATENT DOCUMENTS

| 55397/98 | 8/1998 | (AU) . |
| 2205477 | 11/1997 | (CA) . |
| 0807629 A1 | 5/1997 | (DE) . |
| 0 370 901 | 5/1990 | (EP) . |
| 0 389 861 | 10/1990 | (EP) . |
| 0 807 629 | 11/1997 | (EP) . |
| 0 860 440 | 8/1998 | (EP) . |
| WO 95/14470 | 6/1995 | (WO) . |

OTHER PUBLICATIONS

A.E. Busch et al., "Role of the $I_{SK}$ Protein in the $I_{minK}$ Channel Complex", *Trends in Pharmacological Sciences*, Jan. 1997, (vol. 18), pp. 26–29.

R.M. Soll et al., "N–Sulfonamides of Benzopyran–Related Potassium Channel Openers: Conversion of Glyburide Insensitive Smooth Muscle Relaxants to Potent Smooth Muscle Contractors", *Bioorganic & Medicinal Chemistry Letters*, vol. 4, No. 5, pp. 769–773, 1994.

A.E. Busch et al., "The Novel Class III Antiarrhythmics NE–10064 and NE–10133 Inhibit $I_{SK}$ Channels Expressed in *Xenopus* Oocytes and $I_{KS}$ in Guinea Pig Cardiac Myocytes", *Biochemical and Biophysical Research Communications*, vol. 202, No. 1, 1994, pp. 265–270.

T.J. Colatsky et al., "Potassium Channel Blockers as Antiarrhythmic Drugs", *Drug Development Research*, 33:235–249, (1994).

Suessbrich, H. et al., "Specific blockade of slowly activating $I_{SK}$ channels by chromanols—impact on the role of $I_{SK}$ channels in epithelia", FEBS Letters 396 (1996), p. 271–275.

Lohrmann, E. et al., "A new class of inhibitors of cAMP–mediated Cl⁻ secretion in rabbit colon, acting by the reduction of cAMP–activated K⁺ conductance", Pflügers Arch—Eur. J. Physiol. 429 (1995), p. 517–530.

*Primary Examiner*—John Kight
*Assistant Examiner*—Binta Robinson
(74) *Attorney, Agent, or Firm*—Finnegan, Henderson, Farabow, Garrett and Dunner, L.L.P.

(57) ABSTRACT

Compounds of the formula I

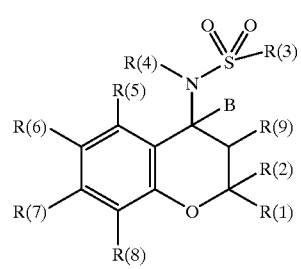

having the meanings of the substituents indicated in the claims are outstandingly efficacious substances for producing medicaments for the prophylaxis and for the therapy of cardiovascular disorders, in particular arrhythmias, for the treatment of ulcers of the gastrointestinal region or for the treatment of diarrheal disorders.

19 Claims, No Drawings

SULFONAMIDE-SUBSTITUTED CHROMANS, PROCESSES FOR THEIR PREPARATION, THEIR USE AS A MEDICAMENT OR DIAGNOSTIC, AND PHARMACEUTICAL PREPARATIONS COMPRISING THEM

This is a continuation of application Ser. No. 09/160,298, filed Sep. 25, 1998, which is incorporated herein by reference now abandoned.

This case claims benefit under 35 U.S.C. □119 of German priority document 19742508.9, filed Sep. 26, 1997, which is hereby incorporated by reference.

BACKGROUND OF THE INVENTION

1. Field of the Invention

The invention relates to compounds of formula I

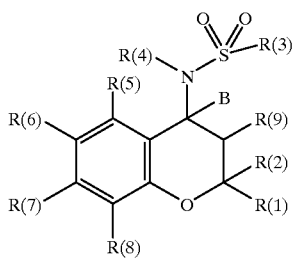

I in which R(1), R(2), R(3), R(4), R(5), R(6), R(7), R(8), R(9), and B have the meanings indicated below, their preparation and their use, in particular in pharmaceuticals. The compounds affect the potassium channel opened by cyclic adenosine monophosphate (cAMP) or the $I_{Ks}$ channel and are outstandingly suitable as pharmaceutical active compounds, for example for the prophylaxis and therapy of cardiovascular disorders, in particular arrhythmias, for the treatment of ulcers of the gastrointestinal area or for the treatment of diarrheal disorders.

In pharmaceutical chemistry, in recent years the 4-acylaminochroman derivatives class has been worked on intensively. The most prominent representative of this class is cromakalim of the formula A (J. Med. Chem. 1986, 29, 2194).

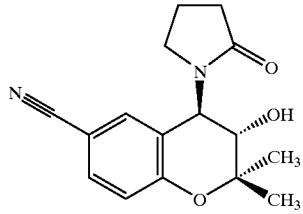

A

Cromakalim and other related 4-acylaminochroman derivatives are compounds having a relaxant action on smooth muscular organs, so they are used for lowering raised blood pressure as a result of vascular muscle relaxation and in the treatment of asthma as a result of relaxation of the smooth musculature of the airways. It is common to all these preparations that they act at the cellular level, for example, of smooth muscle cells and result there in an opening of certain ATP-sensitive $K^+$ channels. The increase in negative charge in the cell (hyperpolarization) induced by the efflux of $K^+$ ions counteracts the increase in the intracellular $Ca^{2+}$ concentration via secondary mechanisms and thus cell activation, which leads, for example, to muscle contraction.

The compounds of the formula I according to the invention differ from these acylamino derivatives structurally, inter alia, by the replacement of the acylamino group by a sulfonylamino function. While cromakalim (formula A) and analogous acylamino compounds act as openers of ATP-sensitive $K^+$ channels, the compounds of the formula I according to the invention having the sulfonylamino structure, however, do not show any opening action on this $K^+(ATP)$ channel, but surprisingly show a strong and specific blocking (closing) action on a $K^+$ channel which is opened by cyclic adenosine monophosphate (cAMP) and differs fundamentally from the $K^+(ATP)$ channel mentioned. More recent investigations show that this $K^+(CAMP)$ channel identified in colonic tissue is very similar, perhaps even identical, to the $I_{Ks}$ channel identified in the cardiac muscle. In fact, the compounds of the formula I according to the invention were able to show a strong blocking action on the $I_{Ks}$ channel in guinea-pig cardiomyocytes and also on the $I_{sK}$ channel expressed in Xenopus oocytes. As a result of this blocking of the $K^+(cAMP)$ channel or of the $I_{Ks}$ channel, the compounds according to the invention display pharmacological actions of high therapeutic utility in the living body.

Apart from the abovementioned cromakalim or acylaminochroman derivatives, compounds having a 4-sulfonylaminochroman structure, which, however, differ markedly from the compounds of the formula I according to the invention both in the structure and in the biological action, are also described in the literature. Thus EP-A-315 009 describes chroman derivates having a 4-phenylsulfonylamino structure, which are distinguished by antithrombotic and antiallergic properties. EP-A-389 861 and JP 01294677 describe 3-hydroxychroman or chromene derivatives having a cyclic 4-sulfonylamino group (e.g. compound B), which should act as antihypertensives via activation of the $K^+(ATP)$ channels. EP-A-370 901 describes 3-hydroxychroman or chromene derivatives having a 4-sulfonylamino group, the remaining valency of the N atom bearing a hydrogen atom, which have CNS actions. Further 4-sulfonylaminochroman derivatives are described in Bioorg. Med. Chem. Lett. 4 (1994), 769–773: "N-sulfonamides of benzopyran-related potassium channel openers: conversion of glyburyde insensitive smooth muscle relaxants to potent smooth muscle contractors" and in FEBS Letters 396 (1996), 271–275: "Specific blockade of slowly activating $I_{sK}$ channels by chromanols . . . " and Pflügers Arch.—Eur. J. Physiol. 429 (1995), 517–530: "A new class of inhibitors of cAMP-mediated $Cl^-$ secretion in rabbit colon, acting by the reduction of cAMP-activated $K^+$ conductance".

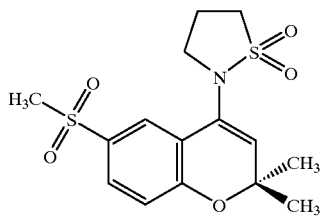

B

DETAILED DESCRIPTION OF THE INVENTION

The present invention relates to compounds of the formula I

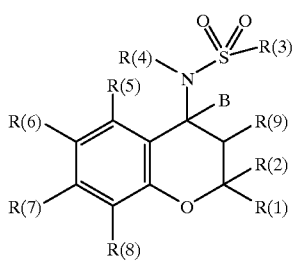

in which:
R(1) and R(2) independently of one another are hydrogen, $CF_3$, $C_2F_5$, $C_3F_7$, alkyl having 1, 2, 3, 4, 5 or 6 carbon atoms, or phenyl, where phenyl is substituted or unsubstituted by 1 or 2 substituents, which are F, Cl, Br, I, $CF_3$, $NO_2$CN, $NH_2$, OH, methyl, ethyl, methoxy, dimethylamino, sulfamoyl, methylsulfonyl, or methylsulfonylamino;

or
R(1) and R(2) together are an alkylene chain having 2, 3, 4, 5, 6, 7, 8, 9, or 10 carbon atoms;
R(3) is R(10)—$C_nH_{2n}$—NR(11)— or R(10)—$C_nH_{2n}$—,
where one $CH_2$ group in the groups $C_nH_{2n}$ can be replaced by —O—, —CO—, —S—, —SO—, —$SO_2$— or —NR(12a)—;
R(12a) is hydrogen, methyl, or ethyl;
R(10) is hydrogen, methyl, cycloalkyl having 3, 4, 5, 6, 7, or 8 carbon atoms, $CF_3$, $C_2F_5$ or $C_3F_7$;
n is zero, 1, 2, 3, 4, 5, 6, 7, 8, 9, or 10;
R(11) is hydrogen or alkyl having 1, 2, 3, 4, 5, or 6 carbon atoms;

or
R(10) and R(11) together are a bond, provided n is not smaller than 3;

or
R(3) together with R(4) is an alkylene chain having 3, 4, 5, 6, 7, or 8 carbon atoms,
where one $CH_2$ group of the alkylene chain can be replaced by —O—, —CO—, —S—, —SO—, —$SO_2$— or —NR(12a)—;
R(12a) is hydrogen, methyl, or ethyl;
R(4) is R(13)—$C_rH_{2r}$,
where one $CH_2$ group of the group $C_rH_{2r}$ can be replaced by —O—, —CH=CH—, —C≡C—, —CO—, —CO—O—, —O—CO—, —S—, —SO—, —$SO_2$—, —NR(14)—, or —CONR(14)—;
R(14) is hydrogen, alkyl having 1, 2, or 3 carbon atoms, —$C_yH_{2y}$—OR(12b), —$C_yH_{2y}$—NR(12b)$_2$;
R(12b) is hydrogen, methyl, or ethyl;
y is 2 or 3;
R(13) is H, $CF_3$, $C_2F_5$, $C_3F_7$, cycloalkyl having 3, 4, 5, 6, 7, or 8 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino; R(15) and R(16) independently of one another are hydrogen or alkyl having 1, 2, 3, or 4 carbon atoms;

or
R(15) and R(16) together are a chain of 4 or 5 methylene groups, of which one $CH_2$ group can be replaced by —O—, —S—, —NH—, —N($CH_3$)—, or —N(benzyl)—;
R(17) is hydrogen, alkyl having 1, 2, or 3 carbon atoms, —$C_xH_{2x}$OR(12c);
R(12c) is hydrogen, methyl, or ethyl;
x is 2 or 3;
r is zero, 1, 2, 3, 4, 5, 6, 7, 8, 9, 10, 11, 12, 13, 14, 15, 16, 17, 18, 19, or 20;
at least one of the substituents R(5), R(6), R(7) and R(8) is —Y—$C_sH_{2s}$—R(18), thienyl, furyl, or an N-containing heterocycle having 1, 2, 3, 4, 5, 6, 7, 8, or 9 carbon atoms, where thienyl, furyl and the N-containing heterocycle are unsubstituted or substituted by 1 or 2 substituents which are F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl, or methylsulfonylamino;
Y is —O—, —CO—, —O—CO—, —S—, —SO—, —$SO_2$—, —$SO_2$—O—, —$SO_2$NR(12d)—, —NR(12d)—, or —CONR(12d)—,
where the first atom as written is bonded to the substituted benzene in each of the compounds of the forumia 1;
R(12d) is hydrogen, methyl, or ethyl;
s is 1, 2, 3, 4, 5, or 6;
R(18) is substituted phenyl which carries one or two substituents which are $NO_2$, CN, $NH_2$, N(methyl)$_2$ OH, ethyl, —COOH, —COOmethyl, —COOethyl, —CONH$_2$, or —CON(methyl)$_2$;

or
R(18) is a substituted N-containing heterocycle having 1, 2, 3, 4, 5, 6, 7, 8, or 9 carbon atoms, which carries one or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;

or
R(18) is —OR(19), —$SO_2$R(19), —NR(19)R(20), or —CONR(19)R(20);
R(19) and R(20) independently of one another are $C_tH_{2t}$—R(21);
t is zero, 1, 2, 3, 4, 5, or 6;
R(21) is hydrogen, $CF_3$, $C_2F_5$, $C_3F_7$, cycloalkyl having 3, 4, 5, 6, 7, or 8 carbon atoms, NR(22)R(23), —OR(24), phenyl, thienyl, or an N-containing heterocycle having 1, 2, 3, 4, 5, 6, 7, 8, or 9 carbon atoms,
where phenyl, thienyl and the N-containing heterocycle are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
R(22) and R(23) independently of one another are hydrogen, alkyl having 1, 2, or 3 carbon atoms;

or
R(22) and R(23) together are a chain of 4 or 5 methylene groups, of which one $CH_2$ group can be replaced by —O—, —S—, —NH—, —N($CH_3$)—, or —N(benzyl)—;
R(24) is hydrogen, alkyl having 1, 2, or 3 carbon atoms;

and the remaining of the substituents R(5), R(6), R(7) and R(8) independently of one another are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, $NO_2$, OR(12e), or NR(12e)R(12f);

R(12e) and R(12f) independently of one another are hydrogen or alkyl having 1, 2, 3, or 4 carbon atoms;

R(9) is hydrogen, OR(12g), or OCOR(12g);
R(12g) is hydrogen or alkyl having 1, 2, or 3 carbon atoms;
B is hydrogen;
or
R(9) and B together are a bond;
and their physiologically tolerable salts.

Preferred compounds of the formula I are those in which:
R(1) and R(2) independently of one another are hydrogen, $CF_3$, $C_2F_5$, $C_3F_7$, alkyl having 1, 2, 3, 4, 5, or 6 carbon atoms, or phenyl, where phenyl is unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
or
R(1) and R(2)
together are an alkylene chain having 2, 3, 4, 5, 6, 7, 8, 9, or 10 carbon atoms;
R(3) is R(10)—$C_nH_{2n}$—NR(11— or R(10)—$C_nH_{2n}$—, where one $CH_2$ group in the groups $C_nH_{2n}$ can be replaced by —O—, —CO—, —S—, —SO—, —$SO_2$—, or —NR(12a)—;
R(12a) is hydrogen, methyl, or ethyl;
R(10) is hydrogen, methyl, cycloalkyl having 3, 4, 5, 6, 7, or 8 carbon atoms, $CF_3$, $C_2F_5$, or $C_3F_7$;
n is zero, 1, 2, 3, 4, 5, 6, 7, 8, 9, or 10;
R(11) is hydrogen or alkyl having 1, 2, 3, 4, 5, or 6 carbon atoms;
or
R(10) and R(11)
together are a bond, provided n is not less than 3;
or
R(3) together with R(4)
is an alkylene chain having 3, 4, 5, 6, 7, or 8 carbon atoms, where one $CH_2$ group of the alkylene chain can be replaced by —O—, —CO—, —S—, —SO—, —$SO_2$—, or —NR(12a)—;
R(12a) is hydrogen, methyl, or ethyl;
R(4) is R(13)—$C_rH_{2r}$,
where one $CH_2$ group of the group $C_rH_{2r}$ can be replaced by —O—, —CH=CH—, —C≡C—, —CO—, —CO—O—, —O—CO—, —S—, —SO—, —$SO_2$—, —NR(14)—, or —CONR(14)—;
R(14) is hydrogen, alkyl having 1, 2, or 3 carbon atoms, —$C_yH_{2y}$—OR(12b), —$C_yH_{2y}$—NR(12b)$_2$;
R(12b) is hydrogen, methyl, or ethyl;
y is 2 or 3;
R(13) is H, $CF_3$, $C_2F_5$, $C_3F_7$, cycloalkyl having 3, 4, 5, 6, 7, or 8 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
R(15) and R(16) independently of one another are hydrogen or alkyl having 1, 2, 3, or 4 carbon atoms;
or
R(15) and R(16) together are a chain of 4 or 5 methylene groups, of which one $CH_2$ group can be replaced by —O—, —S—, —NH—, —N($CH_3$)—, or —N(benzyl)—;
R(17) is hydrogen, alkyl having 1, 2, or 3 carbon atoms,
—$C_xH_{2x}$OR(12c);
R(12c) is hydrogen, methyl, or ethyl;
x is 2 or 3;
r is zero, 1, 2, 3, 4, 5, 6, 7, 8, 9, 10, 11, 12, 13, 14, 15, 16, 17, 18, 19, or 20;
R(6) is —Y—$C_sH_{2s}$—R(18), thienyl, furyl, or an N-containing heterocycle having 1, 3, 4, 5, 6, 7, 8, or 9 carbon atoms,
where thienyl, furyl and the N-containing heterocycle are unsubstituted or substituted by 1 or 2 substituents which are F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl, or methylsulfonylamino;
Y is —O—, —CO—, —O—CO—, —S—, —SO—, —$SO_2$—, —$SO_2$—O—, —$SO_2$NR(12d)—, —NR(12d)—, or —CONR(12d)—, where the first atom as written is bonded to the substituted benzene in each of the compounds of the forumla 1;
R(12d) is hydrogen, methyl, or ethyl;
s is 1, 2, 3, 4, 5, or 6;
R(18) is substituted phenyl, which has 1 or 2 substituents which are $NO_2$, CN, $NH_2$, N(methyl)$_2$, OH, ethyl, —COOH, —COOmethyl, —COOethyl, —$CONH_2$, or —CON(methyl)$_2$;
or
R(18) is a substituted N-containing heterocycle having 1, 2, 3, 4, 5, 6, 7, 8, or 9 carbon atoms, which carries one or 2 substituents which are F, Cl, Br, I, $CF_3$, $NO_2$; CN, $NH_2$, OH, methyl, ethyl, methoxy, dimethylamino, sulfamoyl, methylsulfonyl, or methylsulfonylamino;
or
R(18) is —OR(19), —$SO_2$R(19), —NR(19)R(20), or —CONR(19)R(20);
R(19) and R(20)
independently of one another are $C_tH_{2t}$—R(21);
t is zero, 1, 2, 3, 4, 5, or 6;
R(21) is hydrogen, $CF_3$, $C_2F_5$, $C_3F_7$, cycloalkyl having 3, 4, 5, 6, 7, or 8 carbon atoms, NR(22)R(23), —OR(24), phenyl, thienyl, or an N-containing heterocycle having 1, 2, 3, 4, 5, 6, 7, 8, or 9 carbon atoms,
where phenyl, thienyl and the N-containing heterocycle are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
R(22) and R(23) independently of one another are hydrogen, alkyl having 1, 2, or 3 carbon atoms;
or
R(22) and R(23) together are a chain of 4 or 5 methylene groups, of which one $CH_2$ group can be replaced by —O—, —S—, —NH—, —N($CH_3$)—, or —N(benzyl)—;
R(24) is hydrogen, alkyl having 1, 2, or 3 carbon atoms;

R(5), R(7) and R(8) independently of one another are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, OR(12e), or NR(12e)R (12f);
R(12e) and R(12f) independently of one another are hydrogen or alkyl having 1, 2, 3, or 4 carbon atoms;
R(9) is hydrogen, OR(12g), or OCOR(12g);
R(12g) is hydrogen or alkyl having 1, 2, or 3 carbon atoms;
B is hydrogen;
or
R(9) and B
together are a bond;
and their physiologically tolerable salts.

Particularly preferred compounds of the formula I are those in which:
R(1) and R(2) independently of one another are hydrogen, CF$_3$ or alkyl having 1, 2, 3, 4, 5, or 6 carbon atoms;
or
R(1) and R(2) together are an alkylene chain having 2, 3, 4, 5, or 6 carbon atoms;
R(3) is R(10)—C$_n$H$_{2n}$—;
R(10) is methyl, CF$_3$, or C$_2$F$_5$;
n is zero, 1, or 2;
R(4) is R(13)—C$_r$H$_{2r}$, where one CH$_2$ group of the group C$_r$H$_{2r}$ can be replaced by —O—, —CH=CH—, —C≡C—, —CO—, —CO—O—, —O—CO—, —S—, —SO—, —SO$_2$—, —NR(14)—, or —CONR(14)—;
R(14) is hydrogen, alkyl having 1, 2, or 3 carbon atoms, —C$_y$H$_{2y}$—OR(12b), —C$_y$H$_{2y}$NR(12b)$_2$;
R(12b) is hydrogen, methyl, or ethyl;
y is 2 or 3;
R(13) is H, CF$_3$, C$_2$F$_5$, cycloalkyl having 3, 4, 5, 6, or 7 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
R(15) and R(16)
independently of one another are hydrogen or alkyl having 1, 2, 3, or 4 carbon atoms;
or
R(15) and R(16)
together are a chain of 4 or 5 methylene groups, of which one CH$_2$ group can be replaced by —O—, —S—, —NH—, —N(CH$_3$)—, or —N(benzyl)—;
R(17) is hydrogen, alkyl having 1, 2, or 3 carbon atoms, —C$_x$H$_{2x}$OR(12c);
R(12c) is hydrogen, methyl, or ethyl;
x is 2 or 3;
r is 1, 2, 3, 4, 5, 6, 7, 8, 9, 10, 11, or 12;
R(6) is —Y—C$_s$H$_{2s}$—R(18), thienyl, furyl, or an N-containing heterocycle having 1, 2, 3, 4, 5, 6, 7, 8, or 9 carbon atoms, where thienyl, furyl and the N-containing heterocycle are unsubstituted or substituted by 1 or 2 substituents which are F, Cl, Br, CF$_3$, NO$_2$, CN, NH$_2$, OH, methyl, ethyl, methoxy, methylamino, dimethylamino, ethylamino, diethylamino, sulfamoyl, methylsulfonyl, or methylsulfonylamino;

Y is —O—, —CO—, —O—CO—, —S—, —SO—, —SO$_2$—, —SO$_2$—O—, —SO$_2$NR(12d)—, —NR(12d)—, or —CONR(12d)—,
where the first atom as written is bonded to the substituted benzene in each of the compounds of the forumia 1;
R(R12d) is hydrogen, methyl, or ethyl;
s is 1, 2, 3, 4, 5, or 6;
R(18) is substituted phenyl which carries one or two substituents which are NH$_2$, N(methyl)$_2$, OH, ethyl, —COOmethyl, —COOethyl, —CONH$_2$, or —CON(methyl)$_2$;
or
R(18) is a substituted N-containing heterocycle having 1, 2, 3, 4, 5, 6, 7, 8, or 9 carbon atoms which carries one or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
or
R(18) is —OR(19), —NR(19)R(20), —CONR(19)R(20); R(19) and R(20)
independently of one another are C$_t$H$_{2t}$—R(21);
t is zero, 1, 2, 3, 4, 5, or 6;
R(21) is hydrogen, CF$_3$, NR(22)R(23), —OR(24), phenyl, thienyl, or an N-containing heterocycle having 1, 2, 3, 4, 5, 6, 7, 8, or 9 carbon atoms, where phenyl, thienyl and the N-containing heterocycle are unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
R(22) and R(23) independently of one another are hydrogen, alkyl having 1, 2, or 3 carbon atoms;
or
R(22) and R(23) together are a chain of 4 or 5 methylene groups, of which one CH$_2$ group can be replaced by —O—, —S—, —NH—, or —N(CH$_3$)—;
R(24) is hydrogen, alkyl having 1, 2, or 3 carbon atoms;
R(5), R(7), and R(8)
independently of one another are hydrogen, F, Cl, Br, alkyl having 1, 2, 3, 4, or 5 carbon atoms, CN, CF$_3$, NO$_2$, or OR(12e);
R(12e) is alkyl having 1, 2, 3, or 4 carbon atoms;
R(9) is hydrogen or OH;
B is hydrogen;
or
R(9) and B together are a bond;
and their physiologically tolerable salts.

Very particularly preferred compounds of the formula I are those in which: R(1) and R(2) independently of one another are hydrogen, CF$_3$, or alkyl having 1 or 2 carbon atoms;
or
R(1) and R(2) together are an alkylene chain having 2, 3, 4, or 5 carbon atoms;
R(3) is methyl or ethyl;
R(4) is R(13)—C$_r$H$_{2r}$, where one CH$_2$ group of the group C$_r$H$_{2r}$ can be replaced by —O—, —CO—O—, —O—CO—, —NR(14)—, or —CONR(14)—;
R(14) is hydrogen or alkyl having 1 or 2 carbon atoms;
R(13) is hydrogen, CF$_3$, —NR(15)R(16), —CONR (15)R(16), —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, $CF_3$, methyl, methoxy, sulfamoyl, methylsulfonyl, or methylsulfonylamino;

R(15) and R(16) independently of one another are hydrogen or alkyl having 1 or 2 carbon atoms;

or

R(15) and R(16) together are a chain of 4 or 5 methylene groups, of which one $CH_2$ group can be replaced by —O—, —NH— or —N($CH_3$)—;

R(17) is hydrogen or alkyl having 1 or 2 carbon atoms;

r 1, 2, 3, 4, 5, 6, or 7;

R(6) is —Y—$C_sH_{2s}$—R(18), thienyl, furyl, or an N-containing heterocycle having 1, 2, 3, 4, 5, 6, 7, 8, or 9 carbon atoms, where thienyl, furyl and the N-containing heterocycle are unsubstituted or substituted by 1 or 2 substituents which are F, Cl, Br, $CF_3$, methyl, methoxy, methylamino, dimethylamino, ethylamino, diethylamino, sulfamoyl, methylsulfonyl, or methylsulfonylamino;

Y is —O— or —CONR(12d)—, where the first atom as written is bonded to the substituted benzene in each of the compounds of the forumla 1;

R(12d) is hydrogen, methyl, or ethyl;

s is 1, 2, 3, 4, 5, or 6;

R(18) is substituted phenyl which carries 1 or 2 substituents which are $NH_2$, N(methyl)$_2$, OH, —COOmethyl, —COOethyl, —CON(methyl)$_2$;

or

R(18) is a substituted N-containing heterocycle having 1, 2, 3, 4, 5, 6, 7, 8, or 9 carbon atoms which carries 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;

or

R(18) is —OR(19) or —CONR(19)R(20);

R(19) and R(20) independently of one another are $C_tH_{2t}$—R(21);

t is zero, 1, 2, or 3;

R(21) is hydrogen, $CF_3$, NR(22)R(23), —OR(24);

R(22) and R(23) independently of one another are hydrogen, alkyl having 1, 2, or 3 carbon atoms;

or

R(22) and R(23) together are a chain of 4 or 5 methylene groups, of which one $CH_2$ group can be replaced by —O—, —S—, —NH—, or —N($CH_3$)—;

R(24) is hydrogen, alkyl having 1 or 2 carbon atoms;

R(5), R(7) and R(8) are hydrogen;

R(9) is hydrogen or OH;

B is hydrogen;

or

R(9) and B together are a bond;

and their physiologically tolerable salts.

Particularly especially preferred compounds of the formula 1 are futhermore those in which:

R(1) and R(2) are methyl;

R(3) is methyl or ethyl;

R(4) is R(13)—$C_rH_{2r}$, where one $CH_2$ group of the group $C_rH_{2r}$ can be replaced by —O—;

R(13) is hydrogen, $CF_3$;

r is 1, 2, 3, 4, 5, or 6;

R(6) is —Y—$CrH_{2s}$—R(18), thienyl, or an N-containing heterocycle having 1, 2, 3, 4, 5, 6, 7, 8, or 9 carbon atoms, where thienyl and the N-containing heterocycle are unsubstituted or substituted by 1 or 2 substituents which are F, Cl, $CF_3$, methyl, methoxy, dimethylamino, sulfamoyl, methylsulfonyl, or methylsulfonylamino;

Y is —O—;

is 1, 2, 3, 4, 5, or 6;

R(18) is a substituted N-containing heterocycle having 1, 2, 3, 4, 5, 6, 7, 8, or 9 carbon atoms, which carries one or 2 substituents which are F, Cl, $CF_3$, $NO_2$, CN, OH, methyl, methoxy, dimethylamino, sulfamoyl, methylsulfonyl, or methylsulfonylamino;

or

R(18) is —OR(19) or —CONR(19)R(20);

R(19) and R(20) independently of one another are $C_tH_{2t}$—R(21);

t is zero, 1, 2, or 3;

R(21) is hydrogen, $CF_3$, NR(22)R(23), —OR(24);

R(22) and R(23) independently of one another are hydrogen or alkyl having 1 or 2 carbon atoms;

R(24) is hydrogen or alkyl having 1 or 2 carbon atoms;

R(5), R(7) and R(8) are hydrogen;

R(9) is hydrogen;

B is hydrogen;

and their physiologically tolerable salts.

Alkyl radicals and alkylene radicals can be straight-chain or branched. This also applies to the alkylene radicals of the formulae $C_rH_{2r}$, $C_tH_{2t}$, $C_nH_{2n}$ and $C_sH_{2s}$. Alkyl radicals and alkylene radicals can also be straight-chain or branched if they are substituted or are contained in other radicals, (e.g., in an alkoxy radical or in an alkylmercapto radical, or in a fluorinated alkyl radical). Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, and eicosyl. The divalent radicals derived from these radicals, (e.g.) methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc.) are examples of alkylene radicals.

N-containing heterocycles having 1, 2, 3, 4, 5, 6, 7, 8, or 9 carbon atoms are, in particular, the aromatic systems 1-, 2-, or 3- pyrrolyl, 1-, 2-, 4-, or 5-imidazolyl, 1-, 3-, 4-, or 5-pyrazolyl, 1,2,3-triazol-1-, -4-, or -5-yl, 1,2,4-triazol-1-, -3-, or -5-yl, 1-, or 5-tetrazolyl, 2-, 4-, or 5-oxazolyl, 3-, 4-, or 5-isoxazolyl, 1,2,3-oxadiazol-4-, or -5-yl, 1,2,4-oxadiazol-3-, or -5-yl, 1,3,4-oxadiazol-2-yl, or -5-yl, 2-, 4-, or 5-thiazolyl, 3-, 4-, or 5-isothiazolyl, 1,3,4-thiadiazol-2-, or -5-yl, 1,2,4-thiadiazol-3-, or -5-yl, 1,2,3-thiadiazol-4-, or -5-yl, 2-, 3-, or 4-pyridyl, 2-, 4-, 5-, or 6-pyrimidinyl, 3-, or 4-pyridazinyl, pyrazinyl, 1-, 2-, 3-, 4-, 5-, 6-, or 7-indolyl, 1-, 2-, 4-, or 5-benzimidazolyl, 1-, 3-, 4-, 5-, 6-, or 7-indazolyl, 2-, 3-, 4-, 5-, 6-, 7-, or 8-quinolyl, 1-, 3-, 4-, 5-, 6-, 7-, or 8-isoquinolyl, 2-, 4-, 5-, 6-, 7-, or 8-quinazolinyl, 3-, 4-, 5-, 6-, 7-, or 8-cinnolinyl, 2-, 3-, 5-, 6-, 7- or 8-quinoxalinyl, 1-, 4-, 5-, 6-, 7-or 8-phthalazinyl.

Particularly preferred N-containing heterocycles are pyrrolyl, imidazolyl, quinolyl, pyrazolyl, pyridyl, pyrazinyl, pyrimidinyl, and pyridazinyl.

Thienyl represents both 2- and 3-thienyl. Furyl represents 2- and 3-furyl. Monosubstituted phenyl radicals can be substituted in the 2-, 3- or the 4-position, or disubstituted in the 2,3-, 2,4-, 2,5-, 2,6-, 3,4-, or 3,5-position. The same also applies correspondingly for the N-containing heterocycles or the thiophene radical.

In the case of disubstitution of a radical the substituents can be identical or different.

If the radicals R(1) and R(2) together are an alkylene chain, these radicals with the carbon atom bearing them form a ring which has one carbon atom in common with the 6-membered ring in the formula I, thus a spiro-compound is then present. If R(9) and B together are a bond, a 2H-chromene parent structure is present. If R(10) and R(11) together are a bond, the group R(10)—C$_n$H$_{2n}$—NR(11)— preferably is a nitrogen heterocycle bonded via a nitrogen atom. If R(10) and R(11) together are a bond and the group R(10)—C$_n$H$_{2n}$—NR(11)— is a nitrogen heterocycle bonded via a nitrogen atom, this nitrogen heterocycle is preferably a 4-membered ring or a ring larger than a 4-membered ring, (e.g., a 5-membered ring, 6-membered ring or 7-membered ring).

If the compounds of the formula I contain one or more acidic or basic groups or one or more basic heterocycles, the invention also includes the corresponding physiologically or toxicologically tolerable salts, in particular the pharmaceutically utilizable salts. Thus the compounds of the formula I which bear acidic groups (e.g., one or more COOH groups) can be used, for example, as alkali metal salts, preferably sodium or potassium salts, or as alkaline earth metal salts (e.g., calcium or magnesium salts), or as ammonium salts (e.g. as salts with ammonia or organic amines or amino acids). Compounds of the formula I which bear one or more basic, i.e., protonatable, groups or contain one or more basic heterocyclic rings can also be used in the form of their physiologically tolerable acid addition salts with inorganic or organic acids, for example as hydrochlorides, phosphates, sulfates, methanesulfonates, acetates, lactates, maleates, fumarates, malates, gluconates, etc. If the compounds of the formula I simultaneously contain acidic and basic groups in the molecule, the invention also includes internal salts, so-called betaines, in addition to the salt forms described. Salts can be obtained from the compounds of the formula I according to customary processes, for example by combination with an acid or base in a solvent or dispersant or alternatively from other salts by anion exchange.

In the case of appropriate substitution, the compounds of the formula I can be present in stereoisomeric forms. If the compounds of the formula I contain one or more centers of asymmetry, these can independently of one another have the S configuration or the R configuration. The invention includes all possible stereoisomers (e.g., enantiomers or diastereomers), and mixtures of two or more stereoisomeric forms (e.g., enantiomers and/or diastereomers), in any desired ratios. The invention thus relates to enantiomers, for example, in enantiomerically pure form, both as dextro- and as levorotatory antipodes, and also in the form of mixtures of the two enantiomers in different ratios or in the form of racemates. If cis/trans isomerism is present, the invention relates to both the cis form and the trans form and mixtures of these forms. Individual stereoisomers can be prepared, if desired, by resolution of a mixture according to customary methods or, for example, by stereoselective synthesis. If mobile hydrogen atoms are present, the present invention also includes all tautomeric forms of the compounds of the formula I.

The compounds of the formula I can be prepared by different chemical processes, which are likewise included by the present invention. Thus a compound of the formula I, for example, is obtained by a) reacting a compound of the formula II

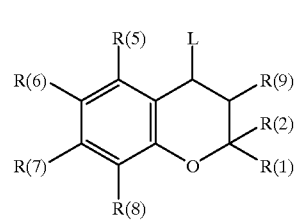

II in which R(1), R(2), R(5), R(6), R(7), R(8), and R(9) have the meanings indicated above and L is a nucleofugic leaving group, in particular Cl, Br, I, methanesulfonyloxy, trifluoromethanesulfonyloxy, or p-toluenesulfonyloxy, in a manner known per se with a sulfonamide or its salt of the formula III

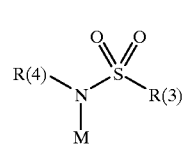

III in which R(3) and R(4) have the meanings indicated above and M is hydrogen or preferably a metal equivalent, particularly preferably lithium, sodium, or potassium;

or by b) reacting a compound of the formula IV

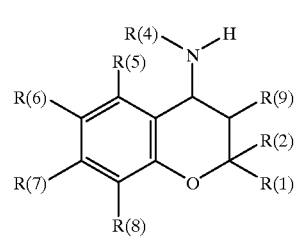

IV in which R(1), R(2), R(4), R(5), R(6), R(7), R(8), and R(9) have the meanings indicated above, with a sulfonic acid derivative of the formula V

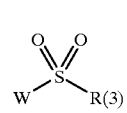

V in which R(3) has the meanings indicated above and W is a nucleofugic leaving group, such as, for example, fluorine, bromine, 1-imidazolyl, but in particular chlorine;

or by c) reacting a compound of the formula VI

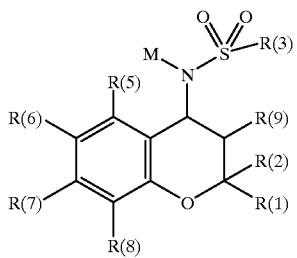

VI in which R(1), R(2), R(3), R(5), R(6), R(7), R(8), R(9), and M have the meanings indicated above, in a manner known per se in the sense of an alkylation reaction with an alkylating agent of the formula VII,

R(4)—L    VII in which R(4) and L have the meanings indicated above;

or by d) carrying out an electrophilic substitution reaction in a compound of the formula I

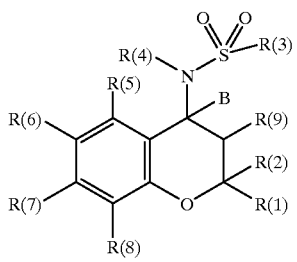

I in which R(1) to R(9) and B have the meanings indicated above, in at least one of the positions R(5), R(6), R(7) and R(8), if this position is hydrogen;

or by e) reacting a compound of the formula VIII

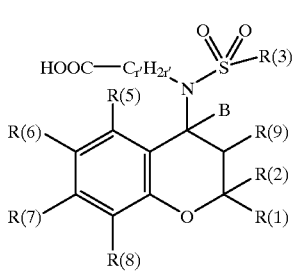

VIII in which R(1), R(2), R(3), R(5), R(6), R(7), R(8), R(9), and B have the meanings indicated above and r' is 1 to 9, with a compound of the formula IX or X

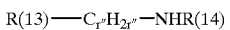    IX

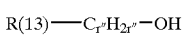    X in which R(13) and R(14) have the meanings indicated above and r" is 1 to 9, in the sense of an esterification or amidation reaction;

or by f) reacting a compound of the formula XII

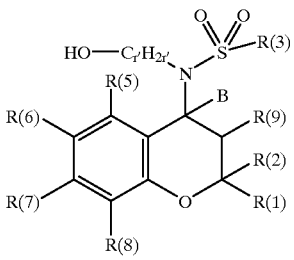

XII in which R(1), R(2), R(3), R(5), R(6), R(7), R(8), R(9), r', and B have the meanings indicated above, with a compound of the formula XIII

    XIII in which R(13), r" and L have the meanings indicated above, in the sense of an alkylation reaction;

or by g) reacting a compound of the formula XIV

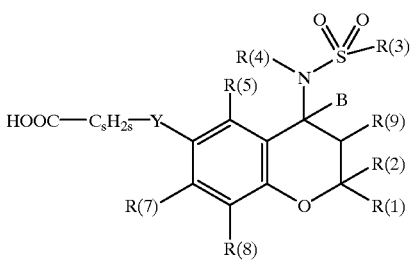

XIV in which R(1), R(2), R(3), R(4), R(5), R(7), R(8), R(9), Y, s, and B have the meanings indicated above, with a compound of the formula HNR(19)R(20), in which R(19) and R(20) have the meanings indicated above, in the sense of an amidation reaction;

or by h) reacting a compound of the formula XV

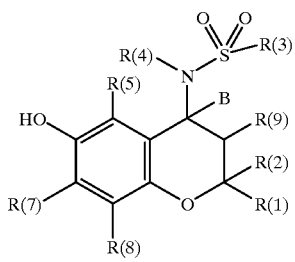

XV in which R(1), R(2), R(3), R(4), R(5), R(7), R(8), R(9), and B have the meanings indicated above, with a compound of the formula R(18)—C$_s$H$_{2s}$—L, in which R(18), s' and L have the meanings indicated above, in the sense of an alkylation reaction;

or by i) reacting a compound of the formula XVI

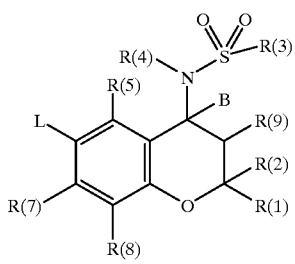

XVI in which R(1), R(2), R(3), R(4), R(5), R(7), R(8), R(9), L, and B have the meanings indicated above, with a compound of the formula Het-Met, in which Het is an N-containing heterocycle having 1, 2, 3, 4, 5, 6, 7, 8, or 9 carbon atoms as well as thienyl or furyl and Met is B(OH)$_2$, trialkylsilyl, an alkali metal cation or an easily substitutable organometallic radical, in the sense of a coupling reaction;

or by j) reacting a compound of the formula XVII,

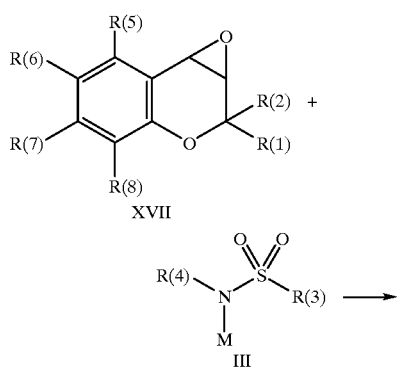

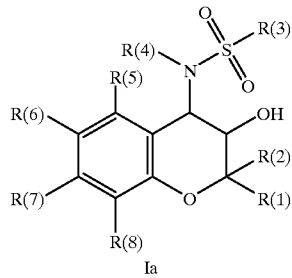

Ia in which R(1), R(2), R(5), R(6), R(7), and R(8) have the meanings indicated above, with a sulfonamide of the formula III in which R(3), R(4), and M have the meanings indicated above or M is advantageously also a trialkylsilyl radical (e.g., a trimethylsilyl radical, to give a chromanol of the formula Ia);

or by k) converting a compound of the formula Ia,

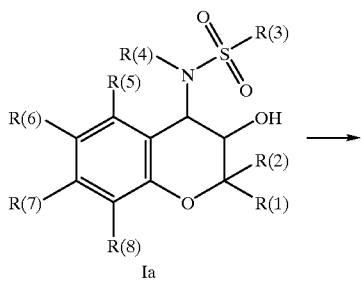

Ia

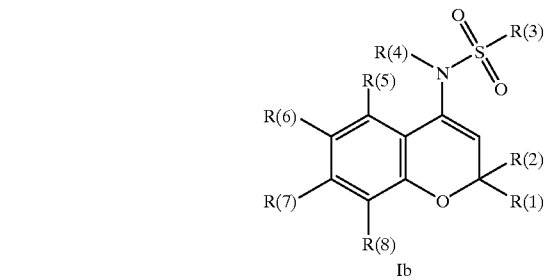

Ib in which R(1) bis R(8) have the meanings indicated above, in the sense of an elimination reaction to give a compound of the formula Ib, in which R(1) to R(8) have the meanings indicated above.

Procedure a) corresponds to the nucleophilic substitution of a leaving group in a reactive bicyclic system of the formula II by a sulfonamide or one of its salts of the formula III. Because of the higher nucleophilicity and higher reactivity of a sulfonamide present in the salt form, when using a free sulfonamide (formula III, M=H), it is preferred to first generate a sulfonamide salt (formula III, M=metal cation) from this by action of a base. If a free sulfonamide (formula III, M=H) is employed, the deprotonation of the sulfonamide to the salt can be carried out in situ. Preferably, those bases are used which are not alkylated or only slightly alkylated themselves, such as, for example, sodium carbonate, potassium carbonate, sterically strongly hindered amines (e.g., dicyclohexylamine, N,N-dicyclohexylethylamine, or other strong nitrogen bases having low nucleophilicity, for example DBU (diazabicycloundecene), N,N',N'''-triisopropylguanidine etc.) However, other customarily used bases can also be employed for the reaction, such as potassium tert-butoxide, sodium methoxide, alkali metal hydrogencarbonates, alkali metal hydroxides, such as, for example, LiOH, NaOH or KOH, or alkaline earth metal hydroxides, such as, for example, Ca(OH)$_2$.

The reaction is preferably carried out in a solvent, particularly preferably in polar organic solvents such as, for example, dimethylformamide (DMF), dimethylacetamide (DMA), dimethyl sulfoxide (DMSO), tetramethylurea, (TMU), hexamethylphosphoramide (HMPA), tetrahydrofuran (THF), dimethoxyethane (DME) or other ethers, or, for example, also in a hydrocarbon such as toluene or in a halogenated hydrocarbon such as chloroform or methylene chloride etc. It is also possible to carry out the reaction, however, in polar protic solvents, such as, for example, in water, methanol, ethanol, isopropanol, ethylene glycol or its oligomers and their corresponding hemiethers or alternatively their ethers. The reaction can also be carried out in mixtures of these solvents. It is likewise also possible to carry out the reaction, however, without solvent. The reaction is preferably carried out in a temperature range from −10 to +140° C., particularly preferably in a range from 20 to 100° C. Conveniently, procedure a) can also be carried out under the conditions of a phase-transfer catalysis.

The compounds of the formula II are obtained according to methods known from the literature, for example from the corresponding alcohols (formula II, L=—OH) by action of hydrogen halide HL (L=Cl, Br, I) or by action of an inorganic acid halide (POCl$_3$, PCl$_3$, PCl$_5$, SOCl$_2$, SOBr$_2$) or by free-radical halogenation of the corresponding chroman derivatives (formula II, L=H) with elemental chlorine or bromine, or with free-radical-activatable halogenating agents such as N-bromosuccinimide (NBS) or SO$_2$Cl$_2$ (sulfuryl chloride) in the presence of a radical chain initiator such as energy-rich light of the visible or ultraviolet wavelength range or by use of a chemical free-radical initiator such as azodiisobutyronitrile.

Procedure b) describes the reaction, which is known per se and frequently used, of a reactive sulfonyl compound of the formula V, in particular of a chlorosulfonyl compound (W=Cl), with an amino derivative of the formula IV to give the corresponding sulfonamide derivative of the formula I. In principle, the reaction can be carried out without solvent, but reactions of this type are in most cases carried out using a solvent.

The reaction is preferably conducted using a polar solvent, preferably in the presence of a base, which can itself be advantageously used as a solvent, (e.g., when using triethylamine, in particular pyridine and its homologs). Solvents likewise used are, for example, water, aliphatic alcohols, (e.g., methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPA). The reaction is in this case carried out at a temperature from 0 to 160° C., preferably from 20 to 100° C.

The amines of the formula IV are obtained in a manner known from the literature, preferably from the corresponding carbonyl compounds of the formula XX,

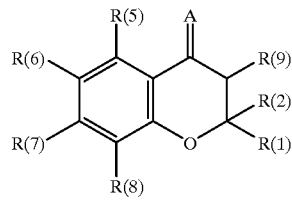

XX in which R(1), R(2), R(5), R(6), R(7), R(8), and R(9) have the meanings indicated above and A is oxygen, either with ammonia or an amine of the formula XXI,

 XXI in which R(4) has the meanings indicated, under reductive conditions or reductive catalytic conditions, preferably at relatively elevated temperature and in an autoclave. In this reaction, primarily by condensation reaction of the ketones of the formula XX (A=oxygen) and the amines of the formula XXI in situ Schiff bases of the formula XX, in which A is R(4)—N= are formed which can be converted immediately, i.e. without prior isolation, into the amines of the formula IV by reduction. However, it is also possible to prepare the Schiff bases (formula XX, A is R(4)—N=) intermediately formed in the condensation reaction from the compounds of the formulae XX and XXI according to methods known from the literature and to first isolate them, in order to then convert them in a separate step using a suitable reductant, such as, for example, NaBH$_4$, LiAlH$_4$, NaBH$_3$CN or by catalytic hydrogenation in the presence of, for example, Raney nickel or a noble metal such as, for example, palladium, into the compounds of the formula IV.

The compounds of the formula IV in which R(4) is hydrogen can advantageously also be obtained in a manner known from the literature by reduction of oximes or oxime ethers (formula XX, A is =N—OR, R=H or alkyl) or hydrazones (formula XX, A is =N—NR$_2$, R is, for example, =H or alkyl) (e.g., using a complex metal hydride or by catalytic hydrogenation). The oximes and hydrazones necessary for this are preferably prepared in a manner known per se from the ketones of the formula XX (A=oxygen) using hydrazine or one of its derivatives or, for example, using hydroxylamine hydrochloride under dehydrating conditions. Particularly advantageously, the compounds of the formula IV in which R(4) is hydrogen can also be obtained by amination using a suitable ammonium compound (e.g., ammonium acetate, in the presence of a suitable reductant, such as, for example, NaCNBH$_3$, (J. Am. Chem. Soc. 93, 1971, 2897)).

Alternatively, the amino derivatives of the formula IV can also be obtained in a manner known per se from the literature by reaction of the reactive compounds of the formula II where R(1), R(2), R(5), R(6), R(7), R(8), R(9), and L have the meaning indicated, either with ammonia or an amine of the formula XX where R(4) has the meaning indicated.

Procedure c) represents the alkylation reaction, which is known per se, of a sulfonamide or of one of its salts VI with an alkylating agent of the formula VII. Corresponding to the analogy of the reaction to procedure a), the reaction conditions already described in detail under procedure a) apply to procedure c). In addition to the bases already mentioned there, sodium hydride or a phosphazene base are preferably used for the deprotonation of the sulfonamide.

The preparation of the sulfonamide derivatives VI (where M=H) and their precursors has already been described in procedure b), where R(4) is then in each case hydrogen. The preparation of the alkylating agent VII is carried out by analogous literature procedures or as described under procedure a), preferably from the corresponding hydroxy compounds (formula VII where L is —OH).

Procedure d) describes the further chemical conversion of compounds of the formula I according to the invention into other compounds of the formula I by electrophilic substitution reactions in one or more of the positions designated by R(5) to R(8), which in each case are hydrogen.

Preferred substitution reactions are 1. aromatic nitration to introduce one or more nitro groups, some or all of which can be reduced to amino groups in subsequent reactions. The amino groups can in turn be converted into other groups in subsequent reactions, for example in a Sandmeyer reaction (e.g., to introduce cyano groups);
2. aromatic halogenation, in particular to introduce chlorine, bromine or iodine;
3. chlorosulfonation (e.g., by action of chlorosulfonic acid to introduce a chlorosulfonyl group, which can be converted into other groups in subsequent reactions, for example, into a sulfonamide group);
4. the Friedel-Crafts acylation reaction to introduce an acyl radical or a sulfonyl radical by action of the corresponding acid chlorides in the presence of a Lewis acid as a Friedel-Crafts catalyst, preferably in the presence of anhydrous aluminum chloride.

Procedure e) describes the esterification of carboxylic acids of the formula VIII with alcohols of the formula X or amidation with amines of the formula IX. Numerous methods have been described in the literature for these reactions. These reactions can be carried out particularly advantageously by activation of the carboxylic acid (e.g., using dicyclohexylcarbodiimide (DCC), if appropriate with addition of hydroxybenzotriazole (HOBT) or dimethylaminopyridine (DMAP), or using O-[(cyano(ethoxycarbonyl)-methylen)amino]-1,1,3,3-tetramethyluronium tetrafluoroborate (TOTU)). However, reactive acid derivatives can also be synthesized first according to known methods (e.g., acid chlorides by reaction of the carboxylic acids of the formula VIII with inorganic acid halides, such as, for example, $SOCl_2$, or acid imidazolides by reaction with carbonyldiimidazole), which are then subsequently reacted, if appropriate with addition of an auxiliary base, with the alcohols or amines of the formula X or IX.

The carboxylic acids of the formula VIII are obtained according to the methods described under a) to d), where, however, R(4) is then in each case —$C_rH_{2r}$COOH or —$C_rH_{2r}$COOalkyl and in the latter case a subsequent hydrolysis of the ester is additionally carried out.

Procedure f describes the alkylation of an alcohol of the formula XII using an alkylating agent of the formula XIII. For this purpose, the alcohol is first converted by action of a suitable base, such as, for example, sodium hydride or a phosphazene base, into an alcoholate salt which is then reacted with the alkylating agent in a suitable polar solvent, such as, for example, dimethylformamide, at temperatures between 20 and 150° C. The deprotonation of the alcohol to the salt can also be carried out in situ, bases then preferably being employed which are not alkylated themselves, such as, for example, potassium carbonate. The alcohols of the formula XII are obtained according to the methods described under a) to d), where then, however, R(4) is in each case —$C_rH_{2r}$OH or —$C_rH_{2r}$OR (R=suitable protective group (e.g., acetoxy) and in the latter case a subsequent removal of the protective group is additionally carried out. However, the alcohols of the formula XII can also be obtained by reduction of the esters of the formula I described under procedure e), in which R(4) is —$C_rH_{2r}$COOalkyl, e.g., with lithium aluminum hydride).

Procedure g) describes the amidation of carboxylic acids of the formula XIV with amines of the formula HNR(19)R(20), which can be carried out under the reaction conditions indicated in procedure e). The carboxylic acids of the formula XIV are obtained, for example, analogously to the method described under procedure h), where then, however, R(18) is COOH or COOalkyl and in the latter case a subsequent hydrolysis of the ester additionally takes place.

Procedure h) corresponds to the alkylation of the phenol of the formula XV with an alkylating agent of the formula R(18)—$C_sH_{2s}$—L, which can be carried out under the reaction conditions already described in procedure f). The phenols of the formula XV can be obtained by the procedure described under a) to f), where then, however, R(6) in each case is an OH group or an appropriately protected derivative (e.g., a benzyl ether), and additionally a removal of the protective group subsequently takes place.

Procedure i) describes the coupling of an aryl halide, e.g. iodide, or of an arylalkyl-sulfonate (e.g., triflate, of the formula XVI with a heterocycle of the formula Het-Met in the presence of a suitable transition metal catalyst. Heterocycles are preferably employed in which the group Met is a boronic acid radical, e.g. $B(OH)_2$, which can be reacted in the sense of a Suzuki coupling with aryl halides of the formula XVI, e.g., in the presence of palladium tetrakis (triphenylphosphine) and of a base such as, for example, potassium carbonate or cesium carbonate. However, heterocycles can also be employed in which the group Met is, for example, a trialkyltin radical (Stille coupling) or a trialkylsilyl radical or alternatively Grignard or organozinc compounds. Appropriate reaction conditions for couplings of this type are described in the literature.

Procedure j) corresponds to the nucleophilic opening of an epoxide of the formula XVII by a sulfonamide or one of its salts of the formula III. The reaction can be carried out under conditions analogous to those described for procedure a). The use of the free sulfonamide in the presence of a substoichiometric amount, e.g. 20–80%, of the corresponding base, e.g., sodium hydride, has proven particularly advantageous. Likewise advantageous is the use of sulfonamide derivatives in which M is a trialkylsilyl radical, e.g. a trimethylsilyl radical, it then being expedient to carry out the reaction in the presence of a fluoride, e.g., tetrabutylammonium fluoride.

The epoxides of the formula XVII are obtained by methods known from the literature from the corresponding olefins of the formula XXII,

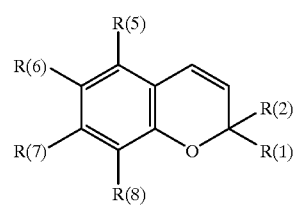

XXII in which R(1), R(2), R(5), R(6), R(7), and R(8) have the meanings indicated above, e.g. by action of a suitable inorganic or organic peroxide, such as, for example, $H_2O_2$ or m-chloroperbenzoic acid, or by base-catalyzed cyclization of the corresponding bromohydrin, which can be obtained from XXII, for example, by reaction with N-bromosuccinimide and water. The epoxides of the formula XVII can also be obtained from the olefins of the formula XXII in optically pure by oxidation in the presence of the chiral Jacobsen catalyst, such as is described, for example, in Tetrahedron Lett. 32, 1991, 5055. The olefins of the formula XXII can be obtained either from the ketones of the formula XX (A=oxygen) by reduction of the carbonyl group to an OH function and subsequent acid-catalyzed elimination or by thermal cyclization of suitably substituted aryl propargyl ethers, such as described, for example, in J. Org. Chem. 38 (1973) 3832.

Procedure k) describes the conversion of a chromanol of the formula Ia into a chromene of the formula Ib by elimination. For this purpose, the chromanol can be subjected to dehydration either directly in the presence of an acid or base or an activation of the hydroxyl group can first be carried out, e.g. by acetylation with acetic anhydride or mesylation with methanesulfonyl chloride, after which a base-catalyzed elimination can subsequently be carried out, e.g., by heating with DBU (diazabicycloundecene).

Apart from the procedures described, a number of other approaches to the compounds of the formula I according to the invention are conceivable. Thus it can be useful, for example, in isolated cases to combine the reactions described under procedures a) to k) with one another in another sequence or, analogously to the methods described, first to prepare compounds not according to the invention in which the radicals R(1) to R(8) have a meaning other than that indicated, and which are then converted into a compound according to the invention in the last stage by a simple conversion of one of the substituents, such as, for example, alkylation, amidation, etc.

In the case of all procedures, it may be appropriate to temporarily protect functional groups in the molecule in certain reaction steps. Such protective group techniques are familiar to the person skilled in the art. The selection of a protective group for groups under consideration and the processes for their introduction and removal are described in the literature and can be adapted to the individual case, if appropriate, without difficulties.

The compounds of the formula I surprisingly have a strong and specific blocking (closing action) on a K$^+$ channel which is opened by cyclic adenosine monophosphate (cAMP) and fundamentally differs from the well-known K$^+$(ATP) channel, and that this K$^+$(cAMP) channel identified in colonic tissue is very similar, perhaps even identical, to the I$_{Ks}$ channel identified in the cardiac muscle. For the compounds according to the invention, it was possible to show a strong blocking action on the I$_{Ks}$ channel in guinea-pig cardiomyocytes and on the I$_{sK}$ channel expressed in Xenopus oocytes. As a result of this blocking of the K$^+$(cAMP) channel or the I$_{Ks}$ channel, the compounds according to the invention display pharmacological actions of high therapeutic utility in the living body and are outstandingly suitable as pharmaceutical active compounds for the therapy and prophylaxis of various syndromes. Thus, the compounds of the formula I are suitable as pharmaceutical compounds for the treatment and prophylaxis of K$^+$ channel-mediated diseases.

Thus the compounds of the formula I according to the invention are distinguished as a novel active compound class of potent inhibitors of stimulated gastric acid secretion. The compounds of the formula I are thus valuable pharmaceutical active compounds for the therapy and prophylaxis of ulcers of the stomach and of the intestinal region, for example of the duodenum. They are likewise suitable on account of their strong gastric secretion-inhibiting action as excellent therapeutics for the. therapy and prophylaxis of reflux esophagitis.

The compounds of the formula I according to the invention are furthermore distinguished by an antidiarrheal action and are therefore suitable as pharmaceutical active compounds for the therapy and prophylaxis of diarrheal disorders.

The compounds of the formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially of cardiac arrhythmias which can be eliminated by action potential prolongation. They can be used especially for the therapy and prophylaxis of atrial fibrillation and atrial flutters and also for the therapy and prophylaxis of reentry arrhythmias and for the prevention of sudden cardiac death as a result of ventricular fibrillation.

Although numerous substances having antiarrhythmic activity are already on the market, there is still no compound which is really satisfactory with respect to activity, range of application and side effects profile, so there is furthermore a need for the development of improved antiarrhythmics. The action of numerous known antiarrhythmics of the so-called class III is based on an increase in the myocardial refractory time due to prolongation of the action potential duration. This is essentially determined by the extent of repolarizing K$^+$ currents which flow out of the cell via various K$^+$ channels. Particularly great importance is ascribed here to the so-called "delayed rectifier" I$_K$, of which two subtypes exist, a rapidly activated I$_{Kr}$ and a slowly activated I$_{Ks}$. Most known class III antiarrhythmics mainly or exclusively block I$_{Kr}$ (e.g., dofetilide, d-sotalol). However, it has been shown that these compounds have an increased proarrhythmic risk at low or normal heart rates, in particular arrhythmias which are designated as "torsades de pointes" being observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging action of the I$_{Kr}$ blockers is markedly reduced, which is attributed to the fact that under these conditions the I$_{Ks}$ contributes more strongly to the repolarization. For these reasons, the substances according to the invention, which act as I$_{Ks}$ blockers, have significant advantages compared with the known I$_{Kr}$ blockers. Meanwhile, it has also been described that a correlation exists between I$_{Ks}$ channel-inhibitory action and the suppression of life-threatening cardiac arrhythmias, such as are induced, for example, by β-adrenergic hyperstimulation (e.g., B. T. J. Colatsky, C. H. Follmer and C. F. Starmer; "Channel Specificity in Antiarrhythmic Drug Action; Mechanism of potassium channel block and its role in suppressing and aggravating cardiac arrhythmias"; Circulation 82 (1990), 2235–2242; A. E. Busch, K. Malloy, W. J. Groh, M. D. Varnum, J. P. Adelman and J. Maylie; "The novel class III antiarrhythmics NE-10064 and NE-10133 inhibit I$_{sK}$ channels in xenopus oocytes and I$_{Ks}$ in guinea pig cardiac myocytes"; Biochem. Biophys. Res. Commun. 202 (1994), 265–270).

Moreover, the compounds contribute to a marked improvement of cardiac insufficiency, in particular of congestive heart failure, advantageously in combination with contraction-promoting (positively inotropic) active substances, e.g. phosphodiesterase inhibitors.

In spite of the therapeutically useful advantages which can be achieved by blockade of the I$_{Ks}$, to date only very few compounds have been described which inhibit this subtype of the "delayed rectifier". The substance azilimide which is in development admittedly has a blocking action on the $I_{Ks}$, but mainly blocks the IKr (selectivity 1:10). WO—A-95/14470 claims the use of benzodiazepines as selective blockers of the $I_{Ks}$. Further $I_{Ks}$ blockers are described in FEBS Letters 396 (1996), 271–275: "Specific blockade of slowly activating $I_{sK}$ channels by chromanols . . . " and Pflügers Arch. —Eur. J. Physiol. 429 (1995), 517–530: "A new class of inhibitors of cAMP-mediated Cl⁻ secretion in rabbit colon, acting by the reduction of cAMP-activated K⁺ conductance". The potency of the 3-hydroxychromanols mentioned there, however, is lower than that of the compounds of the formula I according to the invention.

The compounds of the formula I according to the invention and their physiologically tolerable salts can thus be used in animals, preferably in mammals, and in particular in man as pharmaceuticals per se, as mixtures with one another or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments having K⁺ channel-blocking action. The present invention furthermore relates to pharmaceutical preparations which, as active constituent, contain an efficacious dose of at least one compound of the formula I and/or of a physiologically tolerable salt thereof in addition to customary, pharmaceutically innocuous excipients and auxiliaries. The pharmaceutical preparations normally contain 0.1 to 90 percent by weight of the compounds of the formula I and/or their physiologically tolerable salts. The production of the pharmaceutical preparations can be carried out in a manner known per se. To this end, the compounds of the formula I and/or their physiologically tolerable salts are brought, together with one or more solid or liquid pharmaceutical excipients and/or auxiliaries and, if desired, in combination with other pharmaceutical active compounds, into a suitable administration form or dose form, which can then be used as a pharmaceutical in human medicine or veterinary medicine.

Pharmaceuticals which contain compounds of the formula I according to the invention and/or their physiologically tolerable salts can be administered orally, parenterally, e.g., intravenously, rectally, by inhalation or topically, the preferred administration being dependent on the individual case, e.g., the particular clinical picture of the disorder to be treated.

The person skilled in the art is familiar on the basis of his expert knowledge with the auxiliaries which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solublizers, agents for achieving a depot effect, buffer substances, or colorants.

The compounds of the formula I can also be combined with other pharmaceutical active compounds to achieve an advantageous therapeutic action. Thus in the treatment of cardiovascular disorders, advantageous combinations with substances having cardiovascular activity are possible. Possible advantageous combination components of this type which are advantageous for cardiovascular disorders are, for example, other antiarrhythmics, i.e., class I, class I or class III antiarrhythmics, such as, for example, $I_{Kr}$ channel blockers, e.g. dofetilide, or furthermore hypotensive substances such as ACE inhibitors (for example enalapril, captopril, ramipril), angiotensin antagonists, K⁺ channel activators, and also alpha- and beta-receptor blockers, but also sympathomimetic compounds and compounds having adrenergic activity, as well as Na⁺/H⁺ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with $H_2$ antagonists (e.g., ranitidine, cimetidine, famotidine, etc.), in particular when administered for the treatment of gastrointestinal disorders.

For an oral administration form, the active compounds are mixed with the additives suitable therefor, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, sugar or starch, in particular maize starch. The preparation can take place here both as dry and as moist granules. Suitable oily excipients or solvents are, for example, vegetable or animal oils, such as sunflower oil or cod-liver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds are brought into solution, suspension or emulsion, if desired with the substances customary for this purpose such as solubilizers, emulsifiers or other auxiliaries. The compounds of the formula I and their physiologically tolerable salts can also be lyophilized and the lyophilizates obtained used, for example, for the preparation of injection or infusion preparations. Suitable solvents are, for example, water, physiological saline solution or alcohols, e.g., ethanol, propanol, glycerol, and in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also contain other pharmaceutical auxiliaries such as surfactants, emulsifiers and stabilizers and also a propellant. Such a preparation customarily contains the active compound in a concentration of approximately 0.1 to 10, in particular of approximately 0.3 to 3, % by weight.

The dose of the active compound of the formula I or of the physiologically tolerable salts thereof to be administered depends on the individual case and is to be adapted to the conditions of the individual case for an optimal action as customary. But it depends, of course, on the frequency of administration and on the potency and duration of action of the compound in each employed for therapy or prophylaxis, but also on the nature and severity of the disease to be treated and on the sex, age, weight and individual responsiveness of the human or animal to be treated and on whether the therapy is acute or prophylactic. Customarily, the daily dose of the compound of the formula I in the case of administration to the patient weighing approximately 75 kg is 0.001 mg/kg of body weight to 100 mg/kg of body weight, preferably 0.01 mg/kg of body weight to 20 mg/kg of body weight. The dose can be administered in the form of an individual dose or divided into a number, e.g., two, three, or four, individual doses. In particular when treating acute cases of cardiac arrhythmias, for example in an intensive care unit, a parenteral administration by injection or infusion, e.g., by an intravenous continuous infusion, may be advantageous.

EXPERIMENTAL SECTION

List of abbreviations

| DMA | N,N-dimethylacetamide |
| DMSO | dimethyl sulfoxide |
| EA | ethyl acetate |
| m.p. | melting point |
| in vac. | in vacuo |
| solvt | solvent |
| RT | room temperature |
| THF | tetrahydrofuran |

EXAMPLE 1

N-[6-(3-Ethoxypropoxy)-2,2-dimethylchroman-4-yl]-N-ethyl-methanesulfonamide

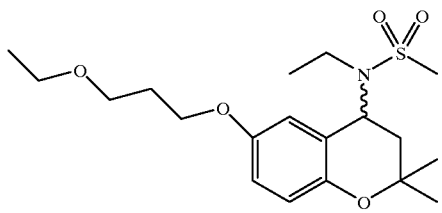

a) 2,2-Dimethyl-6-hydroxychroman-4-one

A reaction mixture of 100 g (0.65 mol) of 2,5-dihydroxyacetophenone in 1 l of acetonitrile, 130 ml (1.55 mol) of pyrrolidine and 290 ml (3.95 mol) of acetone was heated to 45° C. for 8 h. The solvents were then stripped off in vac. and the residue was dissolved in 1 l of EA. The organic phase was washed twice with dilute hydrochloric acid, stirred with activated carbon and dried over magnesium sulfate and largely concentrated. After stirring the residue with petroleum ether and filtering off the precipitate with suction, 102 g of 2,2-dimethyl-6-hydroxychroman-4-one, m.p. 158° C., were obtained.

b) 6-Benzyloxy-2,2-dimethylchroman-4-one 25.2 g (131.2 mmol) of 6-hydroxy-2,2-dimethylchroman-4-one were introduced into 350 ml of diethyl ketone with stirring at RT and, after addition of 18.0 g (131 mmol) of powdered potassium carbonate, stirred at 75° C. for 30 min. After cooling to 60° C., 15.7 ml (131 mmol) of benzyl bromide were added dropwise, the mixture was concentrated in vac. after 2 h, the residue was treated with water and the solid was filtered off with suction, 37 g, m.p. 105–107° C.

c) 6-Benzyloxy-2,2-dimethylchroman-4-one oxime

By heating 11.3 g (40 mmol) of 6-benzyloxy-2,2-dimethylchroman-4-one with 3.1 g (44 mmol) of hydroxylamine hydrochloride in 27 ml of ethanol and 27 ml of pyridine to 70° C. for 3 h, 12.5 g of product, m.p. 105–108° C., were obtained after distilling off the solvt in vac. and precipitating with water. The product was dissolved in EA, dried, concentrated and crystallized using petroleum ether; m.p. 118–120° C.

d) 4-Amino-6-benzyloxy-2,2-dimethylchroman 30 g of 6-benzyloxy-2,2-dimethylchroman-4-one oxime were dissolved in 900 ml of THF/methanol (1:1), treated with 25 ml of aqueous ammonia and hydrogenated in a shaking duck with Raney Ni. The catalyst was then filtered off with suction, the filtrate was concentrated in vac., the residue was dissolved in EA, the solution was dried and concentrated, and the residue was crystallized using petroleum ether, 22.9 g , m.p. 86–88° C.

e) 6-Benzyloxy-4-(methylsulfonyl)amino-2,2-dimethylchroman 4.0 g (14 mmol) of 4-amino-6-benzyloxy-2,2-dimethylchroman were treated with 4.2 ml (30 mmol) of triethylamine at RT in 80 ml of THF and the mixture was stirred for 30 min, then treated with 1.95 g (1.3 ml, 17 mmol) of methanesulfonyl chloride, the temperature rising to 40° C. The mixture was then heated to reflux for 2 h, allowed to stand overnight at RT, concentrated in vac. and the residue was treated with water; 4.9 g of product, m.p. 162–165° C.

f) N-[6-Benzyloxy-2,2-dimethylchroman-4-yl]-N-ethylmethanesulfonamide 7.2 g (20 mmol) of 6-benzyloxy-4-(methylsulfonyl)amino-2,2-dimethylchroman were introduced in portions at 10° C. into a suspension of 0.82 g (27 mmol) of sodium hydride (80 per cent dispersion) in 60 ml of DMA. After stirring at RT for 2 h, 2.2 ml (26.5 mmol) of ethyl iodide were added dropwise, the temperature rising to 32° C. The mixture was then heated to 35–40° C. for 2 h, concentrated in vac., treated with water, the resinous product was taken up EA, the solution was dried and concentrated and the residue was chromatographed using n-heptane/EA (2:1) on silica gel. 6 g of product were crystallized from appropriate fractions using petroleum ether/diisopropyl ether (1:1), m.p. 104–106° C.

g) N-[2,2-Dimethyl-6-hydroxychroman-4-yl]-N-ethylmethanesulfonamide 12 g of N-[6-benzyloxy-2,2-dimethylchroman-4-yl]-N-ethylmethanesulfonamide were dissolved in 250 ml of THF/methanol (1:1) and hydrogenated in a shaking duck using Pd/carbon. After absorption of hydrogen was complete, the catalyst was filtered off with suction, the filtrate was concentrated and the residue was crystallized using diisopropyl ether, 7.7 g, m.p. 169–170° C.

h) 1.5 g (5 mmol) of N-[2,2-dimethyl-6-hydroxychroman-4-yl]-N-ethyl-methanesulfonamide were heated to 80° C. for 30 min with 1.38 g (10 mmol) of powdered potassium carbonate in 60 ml of DMA. 4 ml of 3-ethoxy-1-bromopropane were then added dropwise at 50–60° C., the mixture was heated to 110° C. for 2 h and concentrated in vac. after cooling, the residue was treated with water and aqueous hydrochloric acid, the mixture was extracted with EA, the organic phase was dried and concentrated, and the oily residue was chromatographed on silica gel using n-heptane/EA (2:1). 0.9 g of N-[6-(3-ethoxypropoxy)-2,2-dimethylchroman-4-yl]-N-ethyl-methanesulfonamide was crystallized from appropriate fractions using petroleum ether, m.p. 72–74° C.

EXAMPLE 2

N-Ethyl-N-[6-(5-hydroxypentyloxy)-2,2-dimethylchroman-4-yl]methanesulfonamide

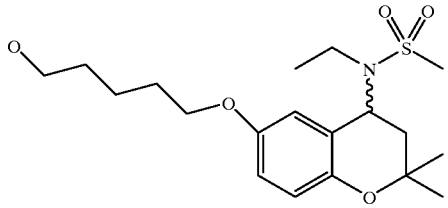

a) Ethyl 4-[4-(ethylmethanesulfonylamino)-2,2-dimethylchroman-6-yloxy]valerate 1.5 g (5 mmol) of N-[2,2-dimethyl-6-hydroxychroman-4-yl]-N-ethylmethane-sulfonamide (Example 1g) were stirred at 80° C. for 30 min with 0.7 g of powdered potassium carbonate in 75 ml of DMA. 0.8 ml (5 mmol) of ethyl 5-bromovalerate was then added and the mixture was stirred at 120° C. for 120 min. After reaction was complete (TLC), the mixture was concentrated in vac., treated with ice water and aqueous hydrochloric acid and a crystalline crude product was obtained, which was chromatographed on silica gel using n-heptane/EA (2:1). Appropriate fractions were crystallized using petroleum ether, 1.5 g, m.p. 65–67° C.

b) 0.35 g (0.8 mmol) of the above compound was reacted with 1.6 ml of a 1M solution of lithium aluminum hydride in THF at 0° C. in 35 ml of anhydrous THF (cf. Example 8).

After working up with EA and concentrating in vac., 0.28 g of the title compound was crystallized using petroleum ether, m.p. 78–80° C.

EXAMPLE 3

5-[4-(Ethylmethanesulfonylamino)-2,2-dimethylchroman-6-yloxy]pentanoic acid (2-methoxyethyl)amide

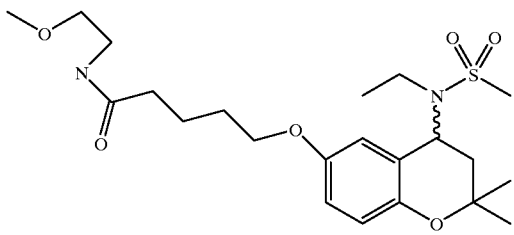

0.6 g of ethyl 4-[4-(ethylmethanesulfonylamino)-2,2-dimethylchroman-6-yloxy]valerate (Example 2a) was heated to reflux for 3 days in 10 ml of methoxyethylamine. The mixture was then concentrated in vac. and the residue was chromatographed on silica gel. 0.28 g of the title compound was crystallized using petroleum ether, m.p. 53–55° C.

EXAMPLE 4

5-[4-(Ethylmethanesulfonylamino)-2,2-dimethylchroman-6-yloxy]pentanoic acid (2-hydroxyethyl)amide

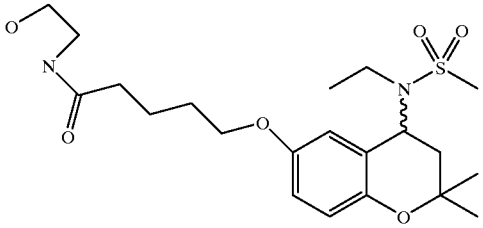

0.2 g of ethyl 4-[4-(ethylmethanesulfonylamino)-2,2-dimethylchroman-6-yloxy]valerate (Example 2a) was heated at a bath temperature of 90° C. for 1 h in 4 ml of 2-hydroxyethylamine. The mixture was then treated with aqueous hydrochloric acid, extracted with EA, dried and concentrated and the residue was crystallized using petroleum ether. 0.16 g of the title compound was obtained, m.p. 88–90° C.

EXAMPLE 5

4-[4-(Ethylmethanesulfonylamino)-2,2-dimethylchroman-6-yloxy]-N-(2-hydroxyethyl)butyramide

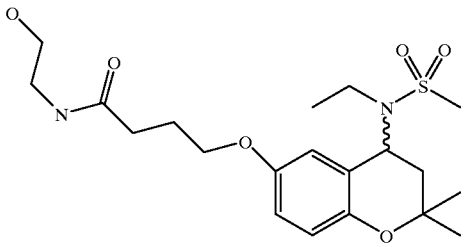

a) Ethyl 4-[4-(ethylmethanesulfonylamino)-2,2-dimethylchroman-6-yloxy]-butyrate 1.0 g (3.3 mmol) of N-[2,2-dimethyl-6-hydroxychroman-4-yl]-N-ethyl-methanesulfonamide (Example 1g) was stirred at 80–90° C. for 30 min with 0.455 g of powdered potassium carbonate in 50 ml of DMA. 0.71 g (0.55 ml, 3.6 mmol) of ethyl 4-bromobutyrate was then added at 60° C. and the mixture was stirred at 115° C. for 90 min. It was then concentrated in vac., the residue was treated with water and aqueous hydrochloric acid, the mixture was taken up in EA, the solution was dried and concentrated, and the residue was chromatographed on silica gel using n-heptane/EA (3:1). Appropriate fractions were crystallized using petroleum ether, 0.74 g, m.p. 40–42° C.

b) 0.2 g of the above butyric acid ester was stirred at a bath temperature of 95° C. in 4 ml of 2-aminoethanol. It was then brought to pH 1 using half-conc. hydrochloric acid with water-cooling, dried and concentrarted, and the residue was dried on an oil pump, and 0.26 g of the oily title compound was obtained.

EXAMPLE 6

2-[4-(Ethylmethanesulfonylamino)-2,2-dimethylchroman-6-yloxy]-N-(2-methoxyethyl) acetamide

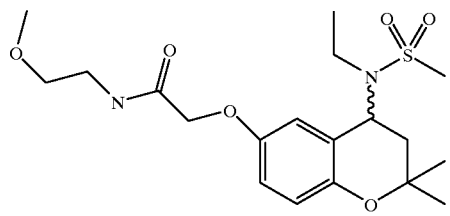

a) Ethyl 4-[4-(ethylmethanesulfonylamino)-2,2-dimethylchroman-6-yloxy]-acetate 1.8 g (6 mmol)) of N-[2,2-dimethyl-6-hydroxychroman-4-yl]-N-ethyl-methanesulfonamide (Example 1g) were stirred at 80–90° C. for 30 min with 0.83 g (6 mmol) of powdered potassium carbonate in 80 ml of DMA. 0.75 ml (6.6 mmol) of ethyl bromoacetate was then added at 60° C. and the mixture was stirred at 110° C. for 90 min. After addition of water, hydrochloric acid, taking up in EA, drying and column chromatography on silica gel, 2.4 g of oily product were obtained.

b) The oily title compound, 0.21 g, was obtained from 0.24 g of the above ester and 3 ml of 2-methoxyethylamine analogously to Example 5b.

EXAMPLE 7

2-[4-(Ethylmethanesulfonylamino)-2,2-dimethylchroman-6-yloxy]—N-(2-hydroxyethyl) acetamide

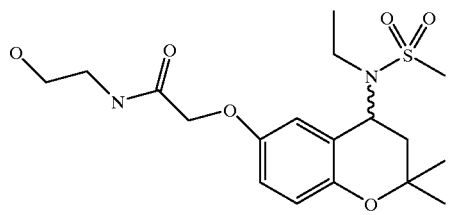

The title compound was obtained by heating 0.23 g of the compound from Example 6a for 1 h in 3 ml of 2-aminoethanol; 0.23 g of oily product.

EXAMPLE 8

N-Ethyl-N-[6-(2-hydroxyethoxy)-2,2-dimethylchroman-4-yl]-methanesulfonamide

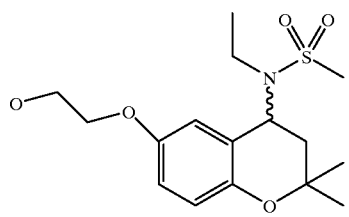

0.77 g (2 mmol) of the compound from Example 5a was treated dropwise with 4 ml of 1M solution of lithium aluminum hydride in THF in 80 ml of anhydrous THF at 0° C. The mixture was then additionally stirred at RT for 1 h, treated with water and dilute hydrochloric acid and concentrated in vac., the residue was extracted with EA, the extract was dried and concentrated, and the residue was crystallized using diisopropyl ether; 0.35 g, m.p. 76–78° C.; from the mother liquor a further 0.3 g of oil.

EXAMPLE 9

N-[6-(2-Ethoxyethoxy)-2,2-dimethylchroman-4-yl]-N-ethylmethanesulfonamide

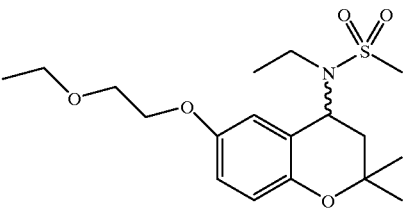

2.3 g (6.7 mmol) of N-ethyl-N-[6-(2-hydroxyethoxy)-2,2-dimethylchroman-4-yl]methanesulfonamide (Example 8) were alkylated with 0.48 g (about 10 mmol) of NaH (80 percent dispersion) and 1.6 ml (about 20 mmol) of ethyl iodide in 50 ml of DMA under nitrogen. After working up and purification by column chromatography on silica gel, 1.0 g of the title compound was crystallized from corresponding fractions using petroleum ether, m.p. 73–75° C.

EXAMPLE 10

N-Ethyl—N-[6-(((4-methoxypyridin-2-yl)methyl)oxy)-2,2-dimethylchroman-4-yl]methanesulfonamide

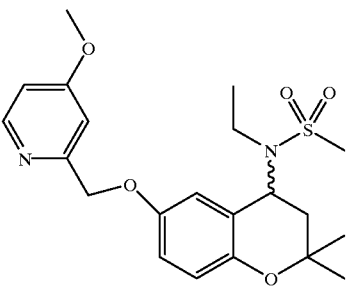

0.58 g (1.9 mmol) of N-[2,2-dimethyl-6-hydroxychroman-4-yl]-N-ethyl-methanesulfonamide (Example 1g) was stirred at 50° C. for 30 min with 0.15 g (5 mmol) of NaH (80%) in 40 ml of DMA. A solution of 0.4 g (2 mmol) of 4-methoxy-2-chloromethylpyridine hydrochloride in 5 ml of DMA was then added dropwise and the mixture was heated to 75° C. for 2 h. After reaction was complete, it was concentrated in vac., the residue was treated with ice water, the mixture was extracted with EA, the extract was dried and concentrated, and the residue was crystallized using diisopropyl ether. 0.5 g was obtained, m.p. 87–89° C.

EXAMPLE 11

Ethanesulfonic acid [6-(2-hydroxyethoxy)-2,2-dimethylchroman-4-yl]-methylamide

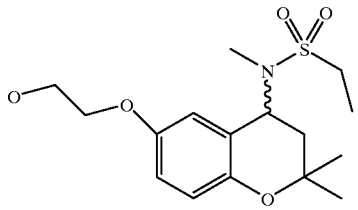

a) 2-Benzyloxy4-(ethylsulfonyl)amino-2,2-dimethylchroman 8.5 g (30 mmol) of 4-amino-6-benzyloxy-2,2-dimethylchroman (Example 1d) were treated with 9 ml (65 mmol) of triethylamine at RT with stirring in 150 ml of THF a nd the mixture was stirr ed for 30 ml, then treated with 3.5 ml (37.5 mmol) of ethanesulfonyl chloride, the temperature rising to 40° C. The mixture was then stirred at 45° C. for 2 h and worked up analogously to Example 1e. 8.8 g of product were obtained, m.p. 145–149° C. (from water).

b) N-[6-Benzyloxy-2,2-dimethylchroman-4-yl]-N-methylethanesulfonamide

Analogously to Example 1f, 8.6 g (23 mmol) of 6-benzyloxy-4-(ethylsulfonyl)amino-2,2-dimethylchroman were introduced in portions into a suspension of 1 g (25 mmol) of sodium hydride (60% dispersion) in 75 ml of DMA at 10° C. After stirring at RT for 2 h, 1.6 ml (25 mmol) of methyl iodide were added dropwise, the temperature rising to 40° C. The mixture was then heated to 35–45° C. for 2 h, and concentrated in vacuo, the residue was treated with water, the resinous product was taken up with EA, the solution was dried and concentrated, and the residue was chromatographed using n-heptane/EA (1:1) on silica gel. 7.4 g of product were crystallized from appropriate fractions using petroleum ether/diisopropyl ether, m.p. 91–93° C.

c) N-[2,2-Dimethyl-6-hydroxychroman-4-yl]-N-methylethanesulfonamide 7.2 g (18.5 mmol) of N-[6-benzyloxy-2,2-dimethylchroman-4-yl]-N-methylethanesulfonamide were dissolved in 150 ml of THF/methanol (1:1) and hydrogenated in a shaking duck using Pd/carbon. After absorption of hydrogen was complete, the catalyst was filtered off with suction, the filtrate was concentrated and the residue was crystallized using diisopropyl ether, 5.0 g, m.p. 160–162° C.

d) Ethyl 4-[4-(methylethanesulfonylamino)-2,2-dimethylchroman-6-yloxy]-acetate 2.1 g (7 mmol) ) of N-[2,2-dimethyl-6-hydroxychroman-4-yl]-N-methylethanesulfonamide were reacted with potassium carbonate and 0.9 ml (8 mmol) of ethyl bromoacetate in DMA analogously to Example 6a. After treating with diisopropyl ether/petroleum ether, 2.5 g of crystalline product were obtained, m.p. 92–94° C.

e) Analogously to Example 8, the title compound was obtained from 1.8 g of the above ester using lithium aluminum hydride. 1.3 g of product crystallized from a little diisopropyl ether, m.p. 89–92° C.

EXAMPLE 12

Ethanesulfonic acid [6-(2-ethoxyethoxy)-2,2-dimethylchroman-4-yl]methylamide

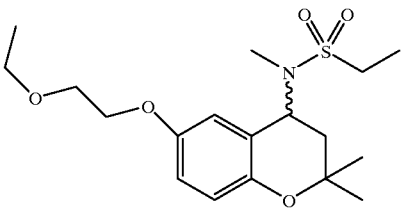

0.5 g of the compound from Ex. 11 was reacted with NaH and ethyl iodide in DMA analogously to Ex. 9. After purification by column chromatography on silica gel, 0.4 g of the title compound was crystallized using petroleum ether, m.p. 70–72° C.

EXAMPLE 13

Methyl 4-[4-(ethanesulfonylmethylamino)-2,2-dimethylchroman-6-foxymethyl]benzoate

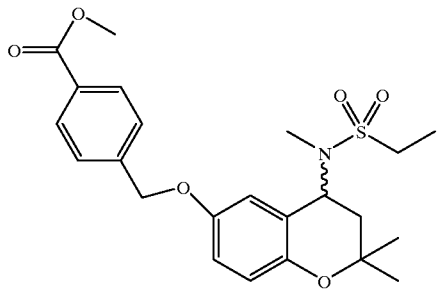

0.6 g (2 mmol) of N-[2,2-dimethyl-6-hydroxyxhroman-4-yl]-N-methylethanesulfonamide (Example 11c) was reacted with powdered potash and then with 0.505 g (2.2 mmol) of 4-(methoxycarbonyl)benzyl bromide in DNA. The product was crystallized using diidopopy ether, 0.72 g, m.p. 86–88° C.

EXAMPLE 14

4-[4-(Ethanesulfonylmethylamino)-2,2imethylchroman-6-yloxymethyl]-benzoic acid

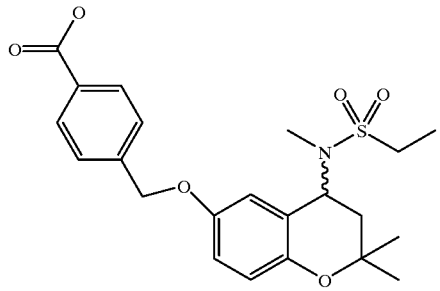

0.6 g of the ester from Example 13 was hydrolyzed at 50° C. for 1 h in 50 ml of 1.5 M methanolic NaOH. The mixture was then concentrated in vac., the residue was treated with water, the mixture was acidified, THF was added until the solution was clear, and the precipitate was filtered off with suction, washed and dried. 0.56 g of the title compound were obtained, m.p. 168–170° C.

EXAMPLE 15

N-[6-(3-Ethoxypropoxy)-2,2-dimethylchroman-4-yl]-N-methylmethanesulfonamide

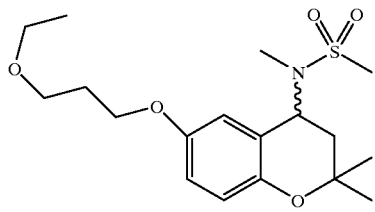

a) N-[6-Benzyloxy-2,2-dimethylchroman-4-yl]-N-methylmethanesulfonamide 8.9 g (25 mmol) of 6-benzyloxy-4-(methylsulfonyl)amino-2,2-dimethylchroman (Ex. 1 e) were introduced in portions at 10° C. into a suspension of 1.2 g (30 mmol) of sodium hydride (60 percent dispersion) in 75 ml of DMA. After stirring at RT for 2 h, 1.9 ml (30 mmol) of methyl iodide were added dropwise, the temperature rising to 50° C. The mixture was then heated to 50° C. for 2 h, concentrated in vac., the residue was treated with water, the resinous product was taken up with EA, the solution was dried and concentrated, and the residue was chromatographed on silica gel using n-heptane/EA (2:1). 7.4 g of product were crystallized from appropriate fractions using petroleum ethen-dusopropyl ether (1:1), m.p. 114–116° C.

b) N-[2,2-Dimethyl-6-hydroxychroman-4-yl]-N-methylmethanesulfonamide 7.3 g of N-[6-benzyloxy-2,2-dimethylchroman-4-yl]-N-methylmethanesulfonamide were dissolved in 100 ml of THF/methanol (1:1) and hydrogenated in a shaking duck using Pd/carbon. After absorpt ion of hydrogen was complete, the catalyst was filtered off with suction, the filtrate was concentrated and the residue was crystallized using dhsopropyl ether/petroleum ether, 5.2 g, m.p. 159–161° C.

c) 0.82 g (2.5 mmol) of N-2,2-dimethyl-6-hydroxychroman-4-yl]-N-methyl-methanesulfonamide was heated to 80° C. for 30 min with 0.83 g (6 mmol) of powdered potassium carbonate in 60 ml of DMA. 2 ml of 3-ethoxy-1-bromopropane were then added dropwise at 50–60° C., the mixture was heated to 110° C. for 3 h and concentrated in vac. after cooling, the residue was treated with water and aqueous hydrochloric acid and extracted with EA, the extract was dried and concentrated, and the oily residue was chromatographed on silica gel using n-heptane/EA (3:1) 0.74 g of the title compound was crystallized from appropriate fractions using petroleum ether, m.p. 61–63° C.

EXAMPLE 16

[6-(2-Hydroxyethoxy)-2,2-dimethylchroman-4-yl]-N-(2-methoxyethyl)-methanesulfonamide

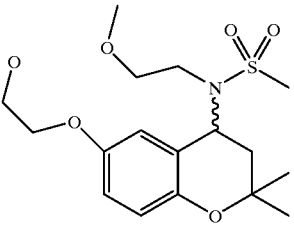

a) N-[6-Benzyloxy-2,2-dimethylchroman-4-yl]-N-(2-methoxyethyl)methanesulfonamide 8.9 g (25 mmol) of 6-benzyloxy-4-(methylsulfonyl)amino-2,2-dimethylchroman (Example 1e) were introduced in portions at 10° C. into a suspension of 0.54 g (30 mmol) of sodium hydride (60% dispersion) in 80 ml of DMA. After stirring at 50° C. for 30 min, 2.2 ml (22 mmol) of 2-methoxyethyl bromide were added dropwise at RT. The mixture was then heated to 110° C. for 1 h, concentrated in vac., the residue was treated with water and aqueous hydrochloric acid, the resinous product was taken up with EA, the solution was dried and concentrated, and the residue was chromatographed on silica gel using toluene/EA (3:1). 2.2 g of product were crystallized from appropriate fractions using petroleum ether, m.p. 66–68° C.

b) N-[2,2-Dimethyl-6-hydroxychroman-4-yl]-N-(2-methoxyethyl)methanesulfonamide 6 g of N-[6-benzyloxy-2,2-dimethylchroman-4-yl]-N-(2-methoxyethyl)methanesulfonamide were dissolved in 100 ml of THF/methanol (1:1) and hydrogenated in a shaking duck using Pd/carbon. The crude product was crystallized using diisopropyl ether, 4.6 g, m.p. 115–117° C.

c) Ethyl 4-[4-((2-methoxyethyl)methanesulfonylamino)-2,2-dimethylchroman-6-yloxy]acetate 2.65 g (8.0 mmol) of N-[2,2-dimethyl-6-hydroxychroman-4-yl]-N-(2-methoxyethyl)methanesulfonamide were heated at 50° C. for 30 min with 0.48 g (10 mmol) of NaH (80%) in 100 ml of DMA. 1.1 ml (10 mmol) of ethyl bromoacetate were then added dropwise analogously to Ex. 6a, the mixture was heated to 100° C. for 1 h and concentrated in vac. after cooling, the residue was treated with water and aqueous hydrochloric acid, the mixture was extracted with EA, the extract was dried and concentrated, and the oily residue was chromatographed on silica gel using n-heptane/EA (1:1). 3.2 g of oily product were obtained.

d) 2.1 g (5 mmol) of the above ester were reduced in 60 ml of THF using 10 ml of 1M lithium aluminum hydride solution in THF. After column chromatography using n-heptane/EA (1:1) on silica gel, 1.4 g of the title compound were crystallized using diisopropyl ether, m.p. 61–63° C.

EXAMPLE 17

N-[6-(2-Ethoxyethoxy)-2,2-dimethylchroman-4-yl]-N-(2-methoxyethyl)methanesulfonamide

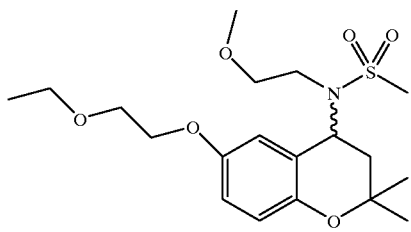

0.56 g (1.5 mmol) of N-[6-(2-hydroxyethoxy)-2,2-dimethylchroman-4-yl]-N-(2-methoxyethyl)methanesulfonamide (Example 16) was reacted with NaH and ethyl iodide in DMA analogously to Example 9. After column chromatography using n-heptane/EA(1:1), 0.32 g of oily product was obtained.

EXAMPLE 18

2-{4-[Methanesulfonyl-(2-methoxyethyl)amino]-2,2-dimethylchroman-6-yloxy}-N-(2-methoxyethyl)acetamide

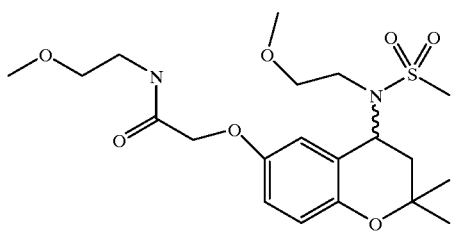

0.43 g of ethyl 4-[4-((2-methoxyethyl)methanesulfonylamino)-2,2-dimethylchroman-6-yloxy]acetate (Example 16c) was heated at 90° C. for 1 h in 6 ml of 2-methoxyethylamine. 0.42 g of oily product were obtained analogously to Examples 5b and 6b.

EXAMPLE 19

N-[6-(4-Hydroxybutoxy)-2,2-dimethylchroman-4-yl]-N-(2-methoxyethyl)methanesulfonamide

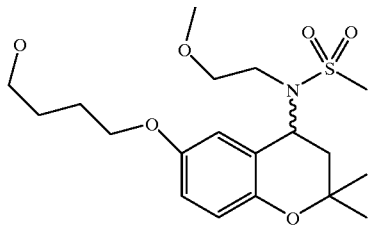

a) Ethyl 4-[4-((2-methoxyethyl)methanesulfonylamino)-2,2-dimethylchroman-6-yloxy]butyrate 2.0 g (6 mmol) of N-[2,2-dimethyt-6-hydroxychroman-4-yl]-N-(2-methoxyethyl)methanesulfonamide (Example 16b) were reacted with potassium carbonate and ethyl 4-bromobutyrate analogously to Example 5a. 2.85 g of oily product were obtained.

b) The title compound was obtained by reducing 0.6 g (1.35 mmol) of the above ester in THF using 2 ml of a 1M solution of lithium aluminum hydride in THF, 0.46 g of oily product.

EXAMPLE 20

N-(2-Hydroxyethyl)-4-{4-[methanesulfonyl-(2-methoxyethyl)amino]-2,2-dimethylchroman-6-yloxy}butyramide

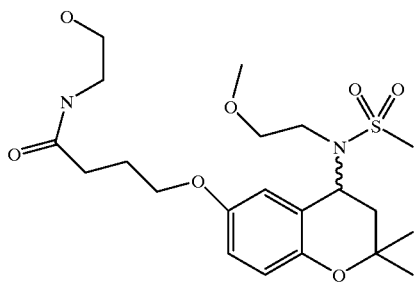

0.55 g of ethyl 4-[4-((2-methoxyethyl)methanesulfonylamino)-2,2-dimethylchroman-6-yloxy]butyrate (Example 19a) was reacted at 90° C. for 2 h in 4 ml of 2-aminoethanol, 0.6 g of oily product.

EXAMPLE 21

N-[6-(3-Ethoxypropoxy)-2,2-dimethylchroman-4-yl]-N-(2-methoxyethyl)methanesulfonamide

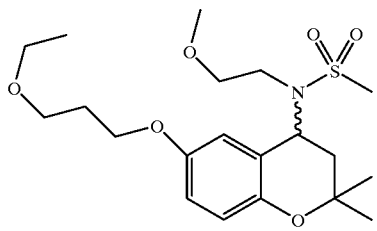

0.5 g (1.5 mmol) of N-[2,2-dimethyl-6-hydroxychroman-4-yl]-N-(2-methoxyethyl)methanesulfonamide (Example 16b) was reacted with potassium carbonate and 3-ethoxy-1-bromopropane analogously to Example 1g. After column chromatography on silica gel using n-heptane/EA(5:1), 0.35 g of oily product was obtained.

EXAMPLE 22

2-[4-(Ethanesulfonyl-(1-propyl)amino)-2,2-dimethylchroman-6-yloxy]-N-(2-methoxyethyl)acetamide

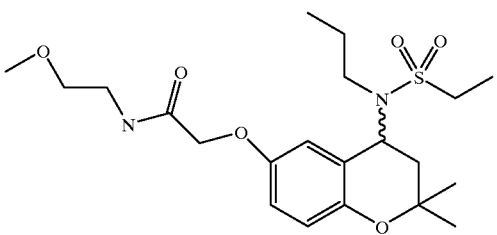

a) N-[6-Benzyloxy-2,2-dimethylchroman-4-yl]-N-(1-propyl)ethanesulfonamide

Analogously to Example 11b, 7.5 g (20 mmol) of 6-benzyloxy-4-(ethylsulfonyl)amino-2,2-dimethylchroman (Example 11a) were introduced in portions at 10° C. into a suspension of 0.82 g (27 mmol) of sodium hydride (80% dispersion) in 100 ml of DMA. After stirring at RT for 2 h, 2.4 ml (26.2 mmol) of 1-propyl bromide were added dropwise. After work-up, the residue was chromatographed on silica gel using n-heptane/EA(1:1) and 6.0 g of product were crystallized from appropriate fractions using petroleum ether, m.p. 102–103° C.

b) N-[2,2-Dimethyl-6-hydroxychroman-4-yl]-N-(1-propyl)ethanesulfonamide 6.0 g of N-[6-benzyloxy-2,2-dimethylchroman-4-yl]-N-(1-propyl)ethanesulfonamide were dissolved in 150 ml of THF/methanol (1:1) and hydrogenated in a shaking duck using Pdlcarbon, 4.4 g of product, m.p. 173–175° C. (from petroleum ether).

c) Ethyl 4-[4-((1-propyl)ethanesulfonylamino)-2,2-dimethylchroman-6-yloxy]acetate 0.72 g (2.2 mmol) of N-[2,2-dimethyl-6-hydroxychroman-4-yl]-N-methylethanesulfonamide was reacted with potassium carbonate and ethyl bromoacetate analogously to Example 6a, 0.47 g of product, m.p. 62–64° C. (from petroleum ether/diisopropyl ether).

d) The title compound was obtained (analogously to Example 6b) from 0.15 g of the above ester using 4 ml of 2-methoxyethylamine (1 h at 90° C.), 0.13 g of product, m.p. 94–95° C. (aqueous hydrochloric acid).

EXAMPLE 23

2-[4-(Ethanesulfonyl-(1-propyl)amino)-2,2-dimethylchroman-6-yloxy]-N-(3-ethoxypropyl)acetamide

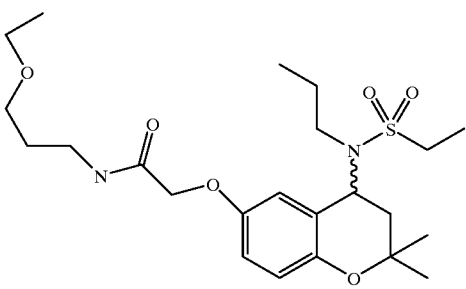

0.15 g of ethyl 4-[4-((1-propyl)ethanesulfonylamino)-2,2-dimethylchroman-6-yloxy]acetate was reacted in 4 ml of 3-ethoxy-1-propylamine (1 h, 95° C.), analogously to Examples 5b) and 6b), 0.16 g of oily product.

EXAMPLE 24

Ethyl 2-[4-(ethanesulfonyl-(1-propyl)amino)-2,2-dimethylchroman-6-yloxy]-N-(2-piperidin-1-yl)acetamide

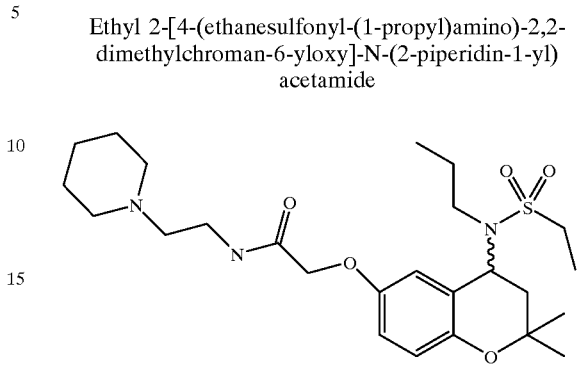

0.19 g (0.45 mmol) of ethyl 4-[4-((1-propyl)ethanesulfonylamino)-2,2-dimethyl-chroman-6-yloxy]acetate (Example 22c) was reacted in 3 ml of N-(2-ethylamino)piperidine (2 h, 100° C.). 0.22 g of the title compound was obtained as a resinous product.

EXAMPLE 25

Ethanesulfonic acid [6-(2-methoxyethoxy)-2,2-dimethylchroman-4-yl]-(1-propyl)amide

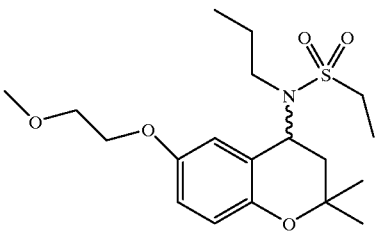

0.491 g (1.5 mmol) of N-[2,2-dimethyl-6-hydroxychroman-4-yl]-N-(1-propyl)ethanesulfonamide (Example 22b) was reacted with NaH and 2-methoxyethyl bromide in DMA. 0.27 g of the title compound was obtained from petroleum ether, m.p. 78–80° C.

EXAMPLE 26

Ethanesulfonic acid (2,2-dimethyl-6-thiophen-2-yl-chroman-4-yl)methylamide

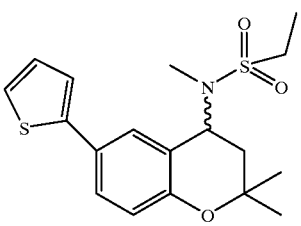

a) 2.83 g (10 mmol) of ethanesulfonic acid (2,2-dimethylchroman-4-yl)methylamide (prepared from 2-hydroxyacetophenone analogously to Examples 1a, c, d to give 4-amino-2,2-dimethylchroman and then analogously to Examples 11a, b) were dissolved in 16 ml of acetic acid and treated dropwise with a solution of 1.62 g (10 mmol) of iodine chloride in 16 ml of acetic acid. After 4 h at RT, the mixture was concentrated and the residue was treated with methylene chloride. The mixture was washed with sodium hydrogencarbonate solution until neutral, dried and the solvent was removed in vacuo. The oil obtained was purified by column chromatography (eluent heptane/EA 1:1), and 1.4 g (34%) of ethanesulfonic acid (6-iodo-2,2-dimethylchroman-4-yl)methylamide were obtained as a solid (m.p. 87–92° C.).

b) 410 mg (1 mmol) of ethanesulfonic acid (6-iodo-2,2-dimethylchroman-4-yl)methylamide were dissolved in 5 ml of toluene and 130 mg (1 mmol) of thiopheneboronic acid, 40 mg of palladium tetrakis(triphenylphosphine) in 5 ml of ethanol and 1.1 ml of 2-molar cesium carbonate solution were added. The mixture was stirred overnight at 80° C. After removing the solvent, the residue was taken up in methylene chloride and washed with water. After drying and removing the solvent, the residue obtained was purified by column chromatography (eluent heptane/ethyl acetate 1:1), and 260 mg (71 %) of ethanesulfonic acid (2,2-dimethyl-6-thiophen-2-yl-chroman-4-yl)methylamide were obtained as an oil.

EXAMPLE 27

N-[6-(3-diethylaminopropoxy)-2,2-dimethylchroman-4-yl]-N-methylmethanesulfonamide

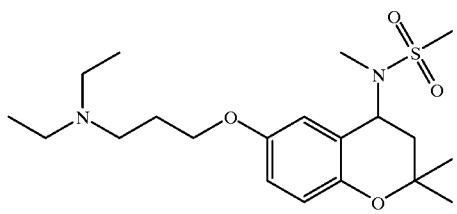

0.7g (2.5 mmol) of N-[2,2-dimethyl-6-hydroxychroman-4-yl]-N-methylmethanesulfonamide (Example 15b) was stirred at RT for 1 h with 1.6 g (5.2 mmol) of phosphazene base [tert-butylimino-tri(pyrrolidino)phosphorane] in 2.5 ml of DMF. 0.48 g (2.6 mmol) of diethylaminopropyl chloride hydrochloride was then added and the mixture was heated to 100° C. for 8 h. After stripping off the solvent in vacuo, the residue was taken up in EA and the mixture was washed with water. After drying over magnesium sulfate and chromatography through a short silica gel column, 0.48 g of N-[6-(3-diethylaminopropoxy)-2,2-dimethylchroman-4-yl]-N-methylmethanesulfonamide was obtained as a glassy solid.

Pharmacological Investigations $I_{sK}$ channels from man, rat or guinea-pig were expressed in Xenopus oocytes. To do this, oocytes were first isolated from Xenopus laevis and defolliculated. $I_{sK}$-encoding RNA synthesized in vitro was then injected into these oocytes. After 2–8 days of $I_{sK}$ protein expression, $I_{sK}$ currents were measured in the oocytes using the two-microelectrode voltage-clamp technique. As a rule, the $I_{sK}$ channels were in this case activated to –10 mV using voltage jumps lasting 15 s. The bath was irrigated with a solution of the following composition: NaCl 96 mM, KCl 2 mM, $CaCl_2$ 1.8 mM, $MgCl_2$ 1 mM, HEPES 5 mM (titrated with NaOH to pH 7.5). These experiments were carried out at room temperature. The following were employed for data acquisition and analysis: Geneclamp amplifier (Axon Instruments, Foster City, USA) and MacLab D/A converter and software (ADlnstruments, Castle Hill, Australia). The substances according to the invention were tested by adding them to the bath solution in different concentrations. The effects of the substances were calculated as the percentage inhibition of the $I_{sK}$ control current, which was obtained when no substance was added to the solution. The data were then extrapolated using the Hill equation in order to determine the inhibitory concentrations $IC_{50}$ for the respective substances.

References

A. E. Busch, H.-G. Kopp, S. Watdegger, I. Samarzija, H. Sußbrich, G. Raber, K. Kunzelmann, J. P. Ruppersberg and F. Lang; "Inhibition of both exogenously expressed $I_{sK}$ and endogenous $K^+$ channels in Xenopus oocytes by isosorbide dinitrate"; J. Physiol. 491 (1995), 735–741;

T. Takumi, H. Ohkubo and S. Nakanishi; "Cloning of a membrane protein that induces a slow voltage-gated potassium current"; Science 242 (1989), 1042–1045;

M. D. Varnum, A. E. Busch, C. T. Bond, J. Maylie and J. P. Adelman; "The minK channel underlies the cardiac potassium current and mediates species-specific responses to protein kinase"; C. Proc. NatI. Acad. Sci. USA 90 (1993), 11528–11532.

For the compounds according to the invention, the following $IC_{50}$ values were determined in the manner described using human $I_{sK}$ protein:

| Compound | $IC_{50}$ [μM] |
|---|---|
| Example 1 | 0.43 |
| Example 2 | 1.71 |
| Example 3 | 6.36 |
| Example 8 | 7.43 |
| Example 9 | 0.69 |
| Example 10 | ~8 |
| Example 15 | 0.32 |
| Example 17 | ~1 |
| Example 21 | 1.74 |
| Example 22 | ~3 |
| Example 23 | 2.49 |
| Example 26 | 0.38 |

We claim:

1. A compound of the formula I,

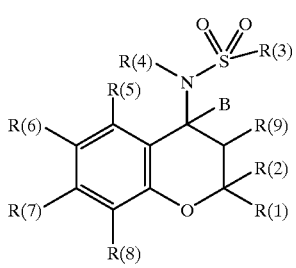

in which:

R(1) and R(2) independently of one another are hydrogen, $CF_3$, $C_2F_5$, $C_3F_7$, alkyl having 1, 2, 3, 4, 5 or 6 carbon atoms, or phenyl, where phenyl is substituted or unsubstituted by 1 or 2 substituents, which are F, Cl, Br, I, $CF_3$, $NO_2$ CN, $NH_2$, OH, methyl, ethyl, methoxy, dimethylamino, sulfamoyl, methylsulfonyl, or methylsulfonylamino;

or

R(1) and R(2) together are an alkylene chain having 2, 3, 4, 5, 6, 7, 8, 9, or 10 carbon atoms;

R(3) is R(10)—$C_nH_{2n}$—NR(11)— or R(10)—$C_nH_{2n}$—,
  where one $CH_2$ group in the groups $C_nH_{2n}$ can be replaced by —O—, —CO—, —S—, —SO—, —$SO_2$— or —NR(12a)—;
  R(12a) is hydrogen, methyl, or ethyl;
  R(10) is hydrogen, methyl, cycloalkyl having 3, 4, 5, 6, 7, or 8 carbon atoms, $CF_3$, $C_2F_5$ or $C_3F_7$;
  n is zero, 1, 2, 3, 4, 5, 6, 7, 8, 9, or 10;
  R(11) is hydrogen or akyl having 1, 2, 3, 4, 5, or 6 carbon atoms;

or

R(10) and R(11) together are a bond, provided n is not smaller than 3;

or

R(3) together with R(4) is an alkylene chain having 3, 4, 5, 6, 7, or 8 carbon atoms,
  where one $CH_2$ group of the alkylene chain can be replaced by —O—, —CO—, —S—, —SO—, —$SO_2$— or —NR(12a)—;
  R(12a) is hydrogen, methyl, or ethyl;

R(4) is R(13)—$C_rH_{2r}$,
  where one $CH_2$ group of the group $C_rH_{2r}$ can be replaced by —O—, —CH=CH—, —C≡C—, —CO—, —CO—O—, —O—CO—, —S—, —SO—, —$SO_2$—, —NR(14)—, or —CONR(14)—;
  R(14) is alkyl having 1, 2, or 3 carbon atoms, —$C_yH_{2y}$—OR(12b), —$C_yH_{2y}$—NR(12b)$_2$;
  R(12b) is hydrogen, methyl, or ethyl;
  y is 2 or 3;

R(13) is H, $CF_3$, $C_2F_5$, $C_3F_7$, cycloalkyl having 3, 4, 5, 6, 7, or 8 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms,
  where phenyl and the N-containing heterocycle are unsubstituted or substituted by I or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
  R(15) and R(16) independently of one another are hydrogen or alkyl having 1, 2, 3, or 4 carbon atoms;

or

R(15) and R(16) together are a chain of 4 or 5 methylene groups, of which one $CH_2$ group can be replaced by —O—, —S—, —NH—, —N($CH_3$)—, or —N(benzyl)—;
  R(17) is hydrogen, alkyl having 1, 2, or 3 carbon atoms, —$C_xH_{2x}$OR(12c);
  R(12c) is hydrogen, methyl, or ethyl;
  x is 2 or 3;
  r is zero, 1, 2, 3, 4, 5, 6, 7, 8, 9, 10, 11, 12, 13, 14, 15, 16, 17, 18, 19, or 20;

at least one of the substituents R(5), R(6), R(7) and R(8) is —Y—$C_sH_{2s}$—R(18), thienyl, furyl, or an N-containing heterocycle having 1, 2, 3, 4, 5, 6, 7, 8, or 9 carbon atoms, where thienyl and the N-containing heterocycle are unsubstituted or substituted by 1 or 2 substituents which are F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl, or methylsulfonylamino;

Y is —O—, —CO—, —O—CO—, —S—, —SO—, —$SO_2$—, —$SO_2$—O—, —$SO_2$NR(12d)—, —NR(12d)—, or —CONR(12d)—,
  where the first atom as written is bonded to the substituted benzene in each of the compounds of the forumia 1;
  R(12d) is hydrogen, methyl, or ethyl;
  s is 1, 2, 3, 4, 5, or 6;

R(18) is substituted phenyl which carries one or two substituents which are $NO_2$, CN, $NH_2$, N(methyl)$_2$, OH, ethyl, —COOH, —COOmethyl, —COOethyl, —CONH$_2$, or —CON(methyl)$_2$;

or

R(18) is a substituted N-containing heterocycle having 1, 2, 3, 4, 5, 6, 7, 8, or 9 carbon atoms, which carries one or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;

or

R(18) is —OR(19), —$SO_2$R(19), —NR(19)R(20), or —CONR(19)R(20);

R(19) and R(20) independently of one another are $C_tH_{2t}$—R(21);
  t is zero, 1, 2, 3, 4, 5, or 6;
  R(21) is hydrogen, $CF_3$, $C_2F_5$, $C_3F_7$, cycloalkyl having 3, 4, 5, 6, 7, or 8 carbon atoms, NR(22)R(23), —OR(24), phenyl, thienyl, or an N-containing heterocycle having 1, 2, 3, 4, 5, 6, 7, 8, or 9 carbon atoms,
    where phenyl, thienyl and the N-containing heterocycle are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, or methylsulfonylamino;
  R(22) and R(23) independently of one another are hydrogen, alkyl having 1, 2, or 3 carbon atoms;

or

R(22) and R(23) together are a chain of 4 or 5 me thylene groups, of which one $CH_2$ group can be replaced by —O—, —S—, —NH—, —N($CH_3$)—, or —N(benzyl)—;
  R(24) is hydrogen, alkyl having 1, 2, or 3 carbon atoms;

and the remaining of the substituents R(5), R(6), R(7) and R(8) independently of one another are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, $NO_2$, OR(12e), or NR(12e)R(12f);
  R(12e) and R(12f) independently of one another are hydrogen or alkyl having 1, 2, 3, or 4 carbon atoms;

R(9) is hydrogen, OR(12g), or OCOR(12g);
  R(12g) is hydrogen or alkyl having 1, 2, or 3 carbon atoms;

B is hydrogen;

or

R(9) and B together are a bond;
or a physiologically tolerable salt thereof.

2. A compound or a salt of the formula I as claimed in claim 1, in which:
R(1) and R(2) independently of one another are hydrogen, $CF_3$, $C_2F_5$, $C_3F_7$, alkyl having 1, 2, 3, 4, 5, or 6 carbon atoms, or phenyl,
  where phenyl is unsubstituted or substituted by 1 or 2 substituents which are F, Cl, Br, I, $CF_3$, $NO_2$, CN, NH$_2$, OH, methyl, ethyl, methoxy, dimethylamino, sulfamoyl, methylsulfonyl, or methylsulfonylamino;

or

R(1) and R(2)
together are an alkylene chain having 2, 3, 4, 5, 6, 7, 8, 9, or 10 carbon atoms;

R(3) is R(10)—C$_n$H$_{2n}$—NR(11)— or R(10)—C$_n$H$_{2n}$—,
where one CH$_2$ group in the groups C$_n$H$_{2n}$ can be replaced by —O—, —CO—, —S—, —SO—, —S$_2$—, or —NR(12a)—;

R(12a) is hydrogen, methyl, or ethyl;

R(10) is hydrogen, methyl, cycloalkyl having 3, 4, 5, 6, 7, or 8 carbon atoms, CF$_3$, C$_2$F$_5$, or C$_3$F$_7$;

n is zero, 1, 2, 3, 4, 5, 6, 7, 8, 9, or 10;

R(11) is hydrogen or alkyl having 1, 2, 3, 4, 5, or 6 carbon atoms;

or

R(10) and R(11)
together are a bond, provided n is not less than 3;

or

R(3) together with R(4)
is an alkylene chain having 3, 4, 5, 6, 7, or 8 carbon atoms, where one CH$_2$ group of the alkylene chain can be replaced by —O—, —CO—, —S—, —SO—, —SO$_2$—, or —NR(12a)—;

R(12a) is hydrogen, methyl, or ethyl;

R(4) is R(13)—C$_r$H$_{2r}$,
where one CH$_2$ group of the group C$_r$H$_{2r}$ can be replaced by —O—, —CH=CH—, —C≡C—, —CO—, —CO—O—, —O—CO—, —S—, —SO—, —SO$_2$—, —NR(14)—, or —CONR(14)—;

R(14) is hydrogen, alkyl having 1, 2, or 3 carbon atoms, —C$_y$H$_{2y}$—OR(12b), —C$_y$H$_{2y}$—NR(12b)$_2$;

R(12b) is hydrogen, methyl, or ethyl;

y is 2 or 3;

R(13) is H, CF$_3$, C$_2$F$_5$, C$_3$F$_7$, cycloalkyl having 3, 4, 5, 6, 7, or 8 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, I, CF$_3$, NO$_2$, CN, NH$_2$, OH, methyl, ethyl, methoxy, dimethylamino, sulfamoyl, methylsulfonyl, or methylsulfonylamino;

R(15) and R(16) independently of one another are hydrogen or alkyl having 1, 2, 3, or 4 carbon atoms;

or

R(15) and R(16) together are a chain of 4 or 5 methylene groups, of which one CH$_2$ group can be replaced by —O—, —S—, —NH—, —N(CH$_3$)—, or —N(benzyl)—;

R(17) is hydrogen, alkyl having 1, 2, or 3 carbon atoms, —C$_x$H$_{2x}$OR(12c);

R(12c) is hydrogen, methyl, or ethyl;

x is 2 or 3;

r is zero, 1, 2, 3, 4, 5, 6, 7, 8, 9, 10, 11, 12, 13, 14, 15, 16, 17, 18, 19, or 20;

R(6) is —Y—C$_s$H$_{2s}$—R(18), thienyl, furyl, or an N-containing heterocycle having 1, 3, 4, 5, 6, 7, 8, or 9 carbon atoms,
where thienyl, furyl and the N-containing heterocycle are unsubstituted or substituted by I or 2 substituents which are F, Cl, Br, I, CF$_3$, NO$_2$, CN, NH$_2$, OH, methyl, ethyl, methoxy, methylamino, dimethylamino, ethylamino, diethylamino, sulfamoyl, methylsulfonyl, or methylsulfonylamino;

Y is —O—, —CO—, —O—CO—, —S—, —SO—, —SO$_2$—, —SO$_2$—O—, —SO$_2$NR(12d)—, —NR(12d)—, or —CONR(12d)—, where the first atom as written is bonded to the substituted benzene in each of the compounds of the forumia 1;

R(12d) is hydrogen, methyl, or ethyl;

s is 1, 2, 3, 4, 5, or 6;

R(18) is substituted phenyl, which has one or two substituents which are NO$_2$, CN, NH$_2$, N(methyl)$_2$, OH, ethyl, —COOH, —COOmethyl, —COOethyl, —CONH$_2$, or —CON(methyl)$_2$;

or

R(18) is a substituted N-containing heterocycle having 1, 2, 3, 4, 5, 6, 7, 8, or 9 carbon atoms, which carries one or 2 substituents which are F, Cl, Br, I, CF$_3$, NO$_2$, CN, NH$_2$, OH, methyl, ethyl, methoxy, dimethylamino, sulfamoyl, methylsulfonyl, or methylsulfonylamino;

or

R(18) is —OR(19), —SO$_2$R(19), —NR(19)R(20), or —CONR(19)R(20);

R(19) and R(20)
independently of one another are C$_t$H$_{2t}$—R(21);

t is zero, 1, 2, 3, 4, 5, or 6;

R(21) is hydrogen, CF$_3$, C$_2$F$_5$, C$_3$F$_7$, cycloalkyl having 3, 4, 5, 6, 7, or 8 carbon atoms, NR(22)R(23), —OR(24), phenyl, thienyl, or an N-containing heterocycle having 1, 2, 3, 4, 5, 6, 7, 8, or 9 carbon atoms,
where phenyl, thienyl and the N-containing heterocycle are unsubstituted or substituted by 1 or 2 substituents which are F, Cl, Br, I, CF$_3$, NO$_2$, CN, NH$_2$, OH, methyl, ethyl, methoxy, dimethylamino, sulfamoyl, methylsulfonyl, or methylsulfonylamino;

R(22) and R(23) independently of one another are hydrogen, alkyl having 1, 2, or 3 carbon atoms;

or

R(22) and R(23) together are a chain of 4 or 5 methylene groups, of which one CH$_2$ group can be replaced by —O—, —S—, —NH—, —N(CH$_3$)—, or —N(benzyl)—;

R(24) is hydrogen, alkyl having 1, 2, or 3 carbon atoms;

R(5), R(7) and R(8) independently of one another are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, OR(12e), or NR(12e)R(12f);

R(12e) and R(12f) independently of one another are hydrogen or alkyl having 1, 2, 3, or 4 carbon atoms;

R(9) is hydrogen, OR(12g), or OCOR(12g);

R(12g) is hydrogen or alkyl having 1, 2, or 3 carbon atoms;

B is hydrogen;

or

R(9) and B
together are a bond.

3. A compound or a salt of the formula I as claimed in claim 1, in which:

R(1) and R(2) independently of one another are hydrogen, CF$_3$ or alkyl having 1, 2, 3, 4, 5, or 6 carbon atoms;

or
R(1) and R(2) together are an alkylene chain having 2, 3, 4, 5, or 6 carbon atoms;
R(3) is R(10)—$C_nH_{2n}$—;
R(10) is methyl, $CF_3$, or $C_2F_5$;
n is zero, 1, or 2;
R(4) is R(13)—$C_rH_{2r}$, where one $CH_2$ group of the group $C_rH_{2r}$ can be replaced by —O—, —CH=CH—, —C≡C—, —CO—, —CO—O—, —O—CO—, —S—, —SO—, —$SO_2$—, —NR(14)—, or—CONR(14)—;
R(14) is hydrogen, alkyl having 1, 2, or 3 carbon atoms, —$C_yH_{2y}$—OR(12b), —$C_yH_{2y}$—NR(12b)$_2$;
R(12b) is hydrogen, methyl, or ethyl;
y is 2 or 3;
R(13) is H, $CF_3$, $C_2F_5$, cycloalkyl having 3, 4, 5, 6, or 7 carbon atoms, —NR(15)R(16), —CONR(15)R(16), —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylarnino;
R(15) and R(16)
independently of one another are hydrogen or alkyl having 1, 2, 3, or 4 carbon atoms;
or
R(15) and R(16)
together are a chain of 4 or 5 methylene groups, of which one $CH_2$ group can be replaced by —O—, —S—, —NH—, —N($CH_3$)—, or —N(benzyl)—;
R(17) is hydrogen, alkyl having 1, 2, or 3 carbon atoms,
—$C_xH_{2x}$OR(12c);
R(12c) is hydrogen, methyl, or ethyl;
x is 2 or 3;
r is 1, 2, 3, 4, 5, 6, 7, 8, 9, 10, 11, or 12;
R(6) is —Y—$C_sH_{2s}$—R(18), thienyl, furyl, or an N-containing heterocycle having 1, 2, 3, 4, 5, 6, 7, 8, or 9 carbon atoms, where thienyl, furyl and the N-containing heterocycle are unsubstituted or substituted by 1 or 2 substituents which are F, Cl, Br, $CF_3$, $NO_2$, CN, $NH_2$, OH, methyl, ethyl, methoxy, methylamino, dimethylamino, ethylamino, diethylamino, sulfamoyl, methylsulfonyl, or methylsulfonylamino;
Y is —O—, —CO—, —O—CO—, —S—, —SO—, —$SO_2$—, —$SO_2$—O—, —$SO_2$NR(12d)—, —NR(12d)—, or —CONR(12d)—,
where the first atom as written is bonded to the substituted benzene in each of the compounds of the fonmia 1;
R(12d) is hydrogen, methyl, or ethyl;
s is 1, 2, 3, 4, 5, or 6;
R(18) is substituted phenyl which carries F or 2 substituents which are $NH_2$, N(methyl)$_2$, OH, ethyl, —COOmethyl, —COOethyl, —$CONH_2$, or —CON(methyl)$_2$;
or
R(18) is a substituted N-containing heterocycle having 1, 2, 3, 4, 5, 6, 7, 8, or 9 carbon atoms which carries one or 2 substituents which are F, Cl, Br, $CF_3$, $NO_2$, CN, $NH_2$, OH, methyl, ethyl, methoxy, dimethylamino, sulfa moyl, methylsulfonyl, or methylsulfonylamino;

or
R(18) is —OR(19), —NR(19)R(20), —CONR(19)R(20);
R(19) and R(20)
independently of one another are $C_tH_{2t}$—R(21);
t is zero, 1, 2, 3, 4, 5, or 6;
R(21) is hydrogen, $CF_3$, NR(22)R(23), —OR(24), phenyl, thienyl, or an N-containing heterocycle having 1, 2, 3, 4, 5, 6, 7, 8, or 9 carbon atoms, where phenyl, thienyl and the N-containing heterocycle are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;
R(22) and R(23) independently of one another are hydrogen, alkyl having 1, 2, or 3 carbon atoms;
or
R(22) and R(23) together are a chain of 4 or 5 methylene groups, of which one $CH_2$ group can be replaced by —O—, —S—, —NH—, or —N($CH_3$)—;
R(24) is hydrogen, alkyl having 1, 2, or 3 carbon atoms;
R(5), R(7), and R(8)
independently of one another are hydrogen, F, Cl, Br, alkyl having 1, 2, 3, 4, or 5 carbon atoms, CN, $CF_3$, $NO_2$, or OR(12e);
R(12e) is alkyl having 1,2,3, or 4 carbon atoms;
R(9) is hydrogen or OH;
B is hydrogen;
or
R(9) and B
together are a bond.
4. A compound or a salt of the formula I as claimed in claim 1, in which:
R(1) and R(2) independently of one another are hydrogen, $CF_3$, or alkyl having 1 or 2 carbon atoms;
or
R(1) and R(2) together are an alkylene chain having 2, 3, 4, or 5 carbon atoms;
R(3) is methyl or ethyl;
R(4) is R(13)—$C_rH_{2r}$, where one $CH_2$ group of the group $C_rH_{2r}$ can be replaced by —O—, —CO—O—, —O—CO—, —NR(14)—, or —CONR(14)—;
R(14) is hydrogen or alkyl having 1 or 2 carbon atoms;
R(13) is hydrogen, $CF_3$, —NR(15)R(16), —CONR(15)R(16), —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, $CF_3$, methyl, methoxy, sulfamoyl, methylsulfonyl, or methylsulfonylamino;
R(15) and R(16) independently of one another are hydrogen or alkyl having 1 or 2 carbon atoms;
or
R(15) and R(16) together are a chain of 4 or 5 methylene groups, of which one $CH_2$ group can be replaced by —O—, —NH—or —N($CH_3$)—;
R(17) is hydrogen or alkyl having 1 or 2 carbon atoms;
r 1, 2, 3, 4, 5, 6, or 7;
R(6) is —Y—$C_sH_{2s}$—R(18), thienyl, furyl, or an N-containing heterocycle having 1, 2, 3, 4, 5, 6, 7, 8, or 9 carbon atoms, where thienyl, furyl and the N-containing heterocycle are unsubstituted or substituted by 1 or 2 substituents which are F, Cl, Br, $CF_3$, methyl, methoxy, methylamino, dimethylamino, ethylamino, diethylamino, sulfamoyl, methylsulfonyl, or methylsulfonylamino;

Y is —O— or —CONR(12d)—, where the first atom as written is bonded to the substituted benzene in each of the compounds of the forumia 1;

R(12d) is hydrogen, methyl, or ethyl;

s is 1, 2, 3, 4, 5, or 6;

R(18) is substituted phenyl which carries 1 or 2 substituents which are $NH_2$, $N(methyl)_2$, OH, —COOmethyl, —COOethyl, —$CON(methyl)_2$;

or

R(18) is a substituted N-containing heterocycle having 1, 2, 3, 4, 5, 6, 7, 8, or 9 carbon atoms which carries 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;

or

R(18) is —OR(19) or —CON R(19)R(20);

R(19) and R(20) independently of one another are $C_tH_{2t}$—R(21);

t is zero, 1, 2, or 3;

R(21) is hydrogen, $CF_3$, NR(22)R(23), —OR(24);

R(22) and R(23) independently of one another are hydrogen, alkyl having 1, 2, or 3 carbon atoms;

or

R(22) and R(23) together are a chain of 4 or 5 methylene groups, of which one $CH_2$ group can be replaced by —O—, —S—, —NH—, or —N($CH_3$)—;

R(24) is hydrogen, alkyl having 1 or 2 carbon atoms;

R(5), R(7) and R(8) are hydrogen;

R(9) is hydrogen or OH;

B is hydrogen;

or

R(9) and B together are a bond.

5. A compound or a salt of the formula I as claimed in claims 1, 2, 3, or 4 in which:

R(1) and R(2) are methyl;

R(3) is methyl or ethyl;

R(4) is R(13)—$C_rH_{2r}$, where one $CH_2$ group of the group $C_rH_{2r}$ can be replaced by —O—;

R(13) is hydrogen, $CF_3$;

r is 1, 2, 3, 4, 5, or 6;

R(6) is —Y—$C_sH_{2s}$—R(18), thienyl, or an N-containing heterocycle having 1, 2, 3, 4, 5, 6, 7, 8, or 9 carbon atoms, where thienyl and the N-containing heterocycle are unsubstituted or substituted by 1 or 2 substituents which are F, Cl, $CF_3$, methyl, methoxy, dimethylamino, sulfamoyl, methylsulfonyl, or methylsulfonylamino;

Y is —O—;

s is 1, 2, 3, 4, 5, or 6;

R(18) is a substituted N-containing heterocycle having 1, 2, 3, 4, 5, 6, 7, 8, or 9 carbon atoms, which carries one or 2 substituents which are F, Cl, $CF_3$, $NO_2$, CN, OH, methyl, methoxy, dimethylamino, sulfamoyl, methylsulfonyl, or methylsulfonylamino;

or

R(18) is —OR(19) or —CONR(19)R(20);

R(19) and R(20) independently of one another are $C_tH_{2t}$—R(21);

t is zero, 1, 2, or 3;

R(21) is hydrogen, $CF_3$, NR(22)R(23), —OR(24);

R(22) and R(23) independently of one another are hydrogen or alkyl having 1 or 2 carbon atoms;

R(24) is hydrogen or alkyl having 1 or 2 carbon atoms;

R(5), R(7) and R(8) are hydrogen;

R(9) is hydrogen;

B is hydrogen.

6. A pharmaceutical composition, comprising a compound of claim 1 and a pharmaceutical carrier.

7. A pharmaceutical composition according to claim 6, further comprising the addition of one or more pharmacologically active compounds.

8. A method for the treatment and prophylaxis of $K^+$ channel-mediated diseases in a patient in need thereof, comprising administering an effective amount of a compound of claim 1 to the patient.

9. A method for inhibiting stimulated gastric acid secretion in a patient in need thereof, comprising administering an effective amount of a compound of claim 1 to the patient.

10. A method for the treatment or prophylaxis of ulcers of the stomach or of the intestinal region in a patient in need thereof, comprising administering an effective amount of a compound of claim 1 to the patient.

11. A method for the treatment or prophylaxis of reflux esophagitis in a patient in need thereof, comprising administering an effective amount of a compound of claim 1 to the patient.

12. A method for the treatment or prophylaxis of diarrhea disorders in a patient in need thereof, comprising administering an effective amount of a compound of claim 1 to the patient.

13. A method for the treatment or prophylaxis of all types of arrythmias in a patient in need thereof, comprising administering an effective amount of a compound of claim 1 to the patient.

14. A method for the treatment or prophylaxis of all types of arrythmias according to claim 13 where the the arrythmias are atrial, ventricular, and supraventricular arrythmias.

15. A method for the treatment or prophylaxis of cardiac arrythmias which can be eliminated by action potential prolongation in a patient in need thereof, comprising administering an effective amount of a compound of claim 1 to the patient.

16. A method for the treatment or prophylaxis of atrial fibrillation or atrial flutters in a patient in need thereof, comprising administering an effective amount of a compound of claim 1 to the patient.

17. A method for the treatment or prophylaxis of reentry arrythmias in a patient in need thereof, comprising administering an effective amount of a compound of claim 1 to the patient.

18. A method for the prevention of sudden cardiac death as a result of ventricular fibrillation in a patient in need thereof, comprising administering an effective amount of a compound of claim 1 to the patient.

19. A method for the treatment of cardiac insufficiency in a patient in need thereof, comprising administering an effective amount of a compound of claim 1 to the patient.

* * * * *

UNITED STATES PATENT AND TRADEMARK OFFICE
CERTIFICATE OF CORRECTION

PATENT NO. : 6,177,449 B1
DATED : January 23, 2001
INVENTOR(S) : Brendel et al.

It is certified that error appears in the above-identified patent and that said Letters Patent is hereby corrected as shown below:

Column 40, claim 1,
Line 64, after "NO$_2$", insert a comma -- , --.

Column 41, claim 1,
Line 39, "I or 2 substituents" should read -- 1 or 2 substituents --.

Column 42, claim 1,
Line 6, "forumia 1" should read -- formula 1 --.
Line 24, "2, 3, 4," should read -- 2, 3, 4, --.
Line 40, "me thylene" should read -- methylene --.

Column 43, claim 2,
Line 9, "-S$_2$-" should read -- -SO$_2$- --.
Line 14, "3," should read -- 3, --.
Line 67, "I or 2 substituents" should read -- 1 or 2 substituents --.

Column 45, claim 3,
Lines 23-24, "methylsulfonylarnino" should read -- methylsulfonylamino --.
Line 54, "fonmia 1" should read -- formula 1 --.
Line 57, "F or 2" should read -- 1 or 2 --.
Line 66, "sulfa moyl" should read -- sulfamoyl --.

Column 46, claim 3,
Line 30, "1, 2, 3," should read -- 1, 2, 3, --.

Column 46, claim 4,
Line 64, after "r", insert -- is --.

Column 47, claim 4,
Line 9, "forumia 1" should read -- formula 1 --.
Line 23, " -CON R(19)R(20)" should read -- CONR(19)R(20) --.

UNITED STATES PATENT AND TRADEMARK OFFICE
CERTIFICATE OF CORRECTION

PATENT NO. : 6,177,449 B1
DATED : January 23, 2001
INVENTOR(S) : Brendel et al.

It is certified that error appears in the above-identified patent and that said Letters Patent is hereby corrected as shown below:

Column 48, claim 5,
Line 6, "$C_tH_{2r}\text{-}R(21)$" should read -- $C_tH_{2t}\text{-}R(21)$ --.

Column 48, claim 12,
Line 36, "diarrhea" should read -- diarrheal --.

Column 48, claim 14,
Line 44, after "where the", delete "the" (second occurrence).

Signed and Sealed this

Eleventh Day of December, 2001

*Attest:*

*Attesting Officer*

NICHOLAS P. GODICI
*Acting Director of the United States Patent and Trademark Office*